United States Patent
Namai et al.

(10) Patent No.: US 9,588,423 B2
(45) Date of Patent: Mar. 7, 2017

(54) ACID DIFFUSION CONTROL AGENT, RADIATION-SENSITIVE RESIN COMPOSITION, RESIST PATTERN-FORMING METHOD, COMPOUND, AND PRODUCTION METHOD

(71) Applicant: JSR CORPORATION, Tokyo (JP)

(72) Inventors: Hayato Namai, Tokyo (JP); Norihiko Ikeda, Tokyo (JP)

(73) Assignee: JSR CORPORATION, Tokyo (JP)

( * ) Notice: Subject to any disclaimer, the term of this patent is extended or adjusted under 35 U.S.C. 154(b) by 57 days.

(21) Appl. No.: 14/541,946

(22) Filed: Nov. 14, 2014

(65) Prior Publication Data

US 2015/0079520 A1  Mar. 19, 2015

Related U.S. Application Data

(63) Continuation of application No. PCT/JP2013/062981, filed on May 8, 2013.

(30) Foreign Application Priority Data

May 17, 2012 (JP) ................................. 2012-113873

(51) Int. Cl.
*G03F 7/039* (2006.01)
*C07C 227/08* (2006.01)
(Continued)

(52) U.S. Cl.
CPC .......... *G03F 7/0045* (2013.01); *C07C 227/08* (2013.01); *C07C 229/08* (2013.01); *C07C 229/12* (2013.01); *C07D 211/14* (2013.01); *C07D 215/04* (2013.01); *C07D 215/06* (2013.01); *C07D 223/10* (2013.01); *C07D 277/60* (2013.01); *C07D 295/108* (2013.01); *C07D 295/15* (2013.01); *C07D 307/20* (2013.01); *C07D 307/94* (2013.01);
(Continued)

(58) Field of Classification Search
CPC ... G03F 7/0045; G03F 7/0397; C07C 229/08; C07C 229/12; C07D 211/14; C07D 215/04; C07D 215/06; C07D 223/10; C07D 295/15; C07D 295/108; C07D 307/20; C07D 307/94; C07D 311/74; C07D 405/06; C07D 411/12
See application file for complete search history.

(56) References Cited

U.S. PATENT DOCUMENTS 4,371,538 A  2/1983 Tsatsas et al.
4,377,689 A  3/1983 Tsatsas et al.
(Continued)

FOREIGN PATENT DOCUMENTS

JP  50-135075 A  10/1975
JP  56-63980 A  5/1981
(Continued)

OTHER PUBLICATIONS

International Search Report issued Aug. 13, 2013 in PCT/JP2013/062981 (with English language translation).
M. Prost, et al., "Dérivés propargyliques VII (1) esters, éthers et carbamates basiques de carbinols propynyliques" Chimica Therapeutica, vol. II, No. 2, 1967, 13 pages.
Jacques Huck, et al., "Enantioselective synthesis of $\beta^2$-amino acids by 1,4-radical addition followed by hydrogen atom transfer" Peptides 2002: Proceeedings of the 27$^{th}$ European Peptide Symposium, 2002, 4 pages.
A. Löffler, et al., "Préparation des α-méthyléne butyrolactones par réaction de Réformatsky; synthése de l'acide protolichéstérinique" Chimia, vol. 23, 1969, 5 pages.
(Continued)

*Primary Examiner* — Anca Eoff
(74) *Attorney, Agent, or Firm* — Oblon, McClelland, Maier & Neustadt, L.L.P.

(57) ABSTRACT

An acid diffusion control agent includes a compound represented by a formula (1), a compound represented by a formula (2) or both thereof. $R^1$ represents a hydrocarbon group comprising a monovalent alicyclic structure, or the like. $R^2$ and $R^3$ each independently represent a monovalent hydrocarbon group, or the like. $R^4$ and $R^5$ each independently represent a monovalent hydrocarbon group, or the like. $R^6$ and $R^7$ each independently represent a monovalent hydrocarbon group, or the like. $R^8$ represents a monocyclic heterocyclic group together with the ester group and with the carbon atom. n is an integer of 1 to 6. $R^9$ represents a monovalent hydrocarbon group, or the like. $R^{10}$ represents a monovalent hydrocarbon group having 1 to 10 carbon atoms. $R^{11}$ and $R^{12}$ each independently represent a monovalent hydrocarbon group, or the like. $R^{13}$ and $R^{14}$ each independently represent a monovalent hydrocarbon group, or the like.

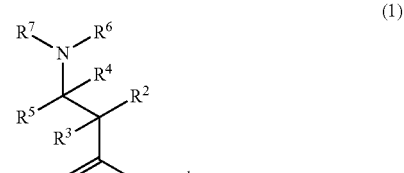

(1)

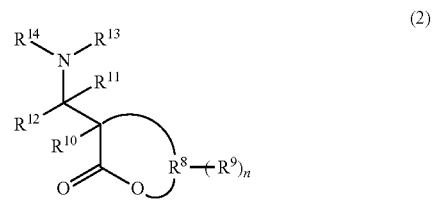

(2)

14 Claims, No Drawings

(51) Int. Cl.

| | | |
|---|---|---|
| *C07C 229/12* | (2006.01) | |
| *G03F 7/004* | (2006.01) | |
| *C07D 307/94* | (2006.01) | |
| *C07D 215/06* | (2006.01) | |
| *C07H 9/04* | (2006.01) | |
| *C07D 493/10* | (2006.01) | |
| *C07D 211/14* | (2006.01) | |
| *C07D 311/74* | (2006.01) | |
| *C07D 223/10* | (2006.01) | |
| *C07D 405/06* | (2006.01) | |
| *C07D 411/12* | (2006.01) | |
| *C07C 229/08* | (2006.01) | |
| *C07D 493/04* | (2006.01) | |
| *C07D 277/60* | (2006.01) | |
| *C07D 295/15* | (2006.01) | |
| *C07D 307/20* | (2006.01) | |
| *C07D 215/04* | (2006.01) | |
| *C07D 295/108* | (2006.01) | |

(52) U.S. Cl.
CPC .......... *C07D 311/74* (2013.01); *C07D 405/06* (2013.01); *C07D 411/12* (2013.01); *C07D 493/04* (2013.01); *C07D 493/10* (2013.01); *C07H 9/04* (2013.01); *G03F 7/0397* (2013.01); *C07C 2103/74* (2013.01)

(56) References Cited

U.S. PATENT DOCUMENTS

| | | |
|---|---|---|
| 4,477,676 A | 10/1984 | Crounse et al. |
| RE42,412 E | 5/2011 | Druzgala et al. |
| 2002/0025970 A1 | 2/2002 | Druzgala et al. |
| 2002/0098443 A1 | 7/2002 | Hatakeyama et al. |
| 2003/0216387 A1 | 11/2003 | Druzgala et al. |
| 2008/0102405 A1 | 5/2008 | Watanabe et al. |
| 2008/0124656 A1* | 5/2008 | Kobayashi ............ C07C 309/00 430/286.1 |
| 2010/0069484 A1 | 3/2010 | Vamvakides |
| 2012/0141938 A1 | 6/2012 | Hatakeyama et al. |

FOREIGN PATENT DOCUMENTS

| | | |
|---|---|---|
| JP | 2002-226470 A | 8/2002 |
| JP | 2002-333714 A | 11/2002 |
| JP | 2002-363148 A | 12/2002 |
| JP | 2003-43678 A | 2/2003 |
| JP | 2003-535128 A | 11/2003 |
| JP | 2006-227632 A | 8/2006 |
| JP | 2006-251672 A | 9/2006 |
| JP | 2007-41146 A | 2/2007 |
| JP | 2008-107513 A | 5/2008 |
| JP | 2010-250076 A | 11/2010 |
| JP | 2012-137729 A | 7/2012 |
| WO | WO 2005/069076 A1 | 7/2005 |
| WO | WO 2006/035790 A1 | 4/2006 |
| WO | WO 2008/087458 A2 | 7/2008 |
| WO | WO 2008/087458 A3 | 7/2008 |

OTHER PUBLICATIONS

Office Action issued Jan. 24, 2017, in Japanese Patent Application No. 2014-515583 (w/ computer-generated English translation).

* cited by examiner

ACID DIFFUSION CONTROL AGENT, RADIATION-SENSITIVE RESIN COMPOSITION, RESIST PATTERN-FORMING METHOD, COMPOUND, AND PRODUCTION METHOD

CROSS-REFERENCE TO RELATED APPLICATIONS

The present application is a continuation application of International Application No. PCT/JP2013/062981, filed May 8, 2013, which claims priority to Japanese Patent Application No. 2012-113873, filed May 17, 2012. The contents of these applications are incorporated herein by reference in their entirety.

BACKGROUND OF THE INVENTION

Field of the Invention

The present invention relates to an acid diffusion control agent, a radiation-sensitive resin composition, a resist pattern-forming method, a compound and a production method.

Discussion of the Background

Upon irradiation with exposure light such as an ArF excimer laser beam or a KrF excimer laser beam, chemically amplified radiation-sensitive resin compositions generate an acid from an acid generating agent at a light-exposed site, and a reaction catalyzed by the acid causes a difference in rates of dissolution in a developer solution between a light-exposed sites and a light-unexposed site, thereby forming a resist pattern on a substrate.

Such radiation-sensitive resin compositions are required to have improved various performances such as resolution along with the advance of microfabrication technologies. To address the demand, an acid diffusion control agent is incorporated in the radiation-sensitive resin composition for the purpose of appropriately controlling diffusion of the acid generated from the acid generating agent. As such an acid diffusion control agent, nitrogen atom-containing compounds having a polar group and a ring structure have been noted, which reportedly increase the resolution and the depth of focus (see Japanese Unexamined Patent Application, Publication Nos. 2002-363148 and 2002-226470).

Under such circumstances, in these days when further miniaturization of resist patterns is advancing, further increase in the resolution and the depth of focus has been demanded, and additionally, a superior line-width-roughness (LWR) performance which is an indicative of a variation of the line width of the resist patterns is also demanded. Moreover, according to the conventional acid diffusion control agent described above, resist patterns formed are likely to be accompanied by top loss, etc., and thus an improvement of the rectangularity of the cross-sectional shape of the resist pattern is also demanded.

SUMMARY OF THE INVENTION

According to one aspect of the present invention, an acid diffusion control agent includes a compound represented by a formula (1), a compound represented by a formula (2) or both thereof.

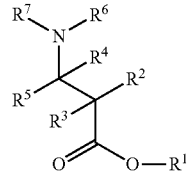

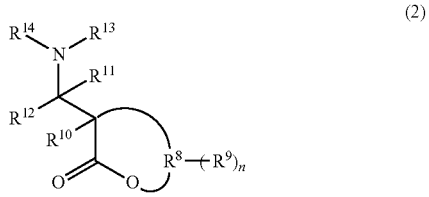

In the formula (1), $R^1$ represents a hydrocarbon group comprising a monovalent alicyclic structure having 3 to 30 carbon atoms, a heteroatom-containing group comprising —O—, —CO—, —COO—, —SO$_2$O—, —NR$^a$SO$_2$—, —NR$^a$CO— or a combination thereof between two carbon atoms in the hydrocarbon group, an aromatic hydrocarbon group having 6 to 30 carbon atoms, or a group obtained by substituting a part or all of hydrogen atoms included in any one of the hydrocarbon group, the heteroatom-containing group or the aromatic hydrocarbon group with a hydroxy group, a halogen atom or a combination thereof, wherein $R^a$ represents a hydrogen atom or a hydrocarbon group having 1 to 10 carbon atoms; $R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms; $R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms together with the nitrogen atom to which $R^6$ and $R^7$ bond. In the formula (2), $R^8$ represents a monocyclic heterocyclic group having a valency of (n+2) and having 5 to 8 ring atoms together with the ester group to which $R^8$ bonds and with the carbon atom to which $R^{10}$ bonds; n is an integer of 1 to 6; $R^9$ represents a monovalent hydrocarbon group having 1 to 20 carbon atoms, a monovalent heteroatom-containing group comprising —O—, —CO—, —COO—, —SO$_2$O—, —NR$^b$SO$_2$, —NR$^b$CO— or a combination thereof between two carbon atoms in the monovalent hydrocarbon group, or a group obtained by substituting a part or all of hydrogen atoms included in any one of the monovalent hydrocarbon group or the monovalent heteroatom-containing group with a hydroxy group, a halogen atom or a combination thereof; and optionally, in a case where n is 2 or greater, two or more $R^9$s among a plurality of $R^9$s taken together represent a ring structure having 3 to 10 ring atoms, a heteroring structure comprising —O—, —CO—, —COO—, —SO$_2$O—, —NR$^b$SO$_2$, —NR$^b$CO— or a combination thereof between two carbon atoms in the ring structure, or a group obtained by substituting a part or all of hydrogen atoms included in any one of the ring structure or the heteroring structure with a hydroxy group, a halogen atom or a combination thereof, wherein $R^b$ represents a hydrogen atom or a monovalent hydrocarbon group having 1 to 10 carbon atoms; $R^{10}$ represents a hydrogen atom or a monovalent hydrocarbon group having 1 to 10 carbon atoms; $R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms together with the nitrogen atom to which $R^{13}$ and $R^{14}$ bond.

According to another aspect of the present invention, a radiation-sensitive resin composition includes a polymer having an acid-labile group, an acid generator; and a first acid diffusion control agent which is the acid diffusion control agent.

According to further aspect of the present invention, a resist pattern-forming method includes providing a resist film using the radiation-sensitive resin composition. The resist film is exposed. The resist film exposed is developed.

According to further aspect of the present invention, a compound is represented by a formula (1).

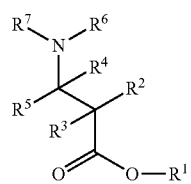

(1)

In the formula (1), $R^1$ represents a hydrocarbon group comprising a monovalent alicyclic structure having 3 to 30 carbon atoms, a heteroatom-containing group comprising —O—, —CO—, —COO—, —SO$_2$O—, —NR$^a$SO$_2$—, —NR$^a$CO— or a combination thereof between two carbon atoms in the hydrocarbon group, an aromatic hydrocarbon group having 6 to 30 carbon atoms, or a group obtained by substituting a part or all of hydrogen atoms included in any one of the hydrocarbon group, the heteroatom-containing group or the aromatic hydrocarbon group with a hydroxy group, a halogen atom or a combination thereof, wherein $R^a$ represents a hydrogen atom or a hydrocarbon group having 1 to 10 carbon atoms; $R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms; $R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms together with the nitrogen atom to which $R^6$ and $R^7$ bond.

According to further aspect of the present invention, a compound is represented by a formula (2).

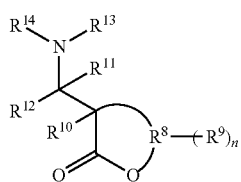

(2)

In the formula (2), $R^8$ represents a monocyclic heterocyclic group having a valency of (n+2) and having 5 to 8 ring atoms together with the ester group to which $R^8$ bonds and with the carbon atom to which $R^{10}$ bonds; n is an integer of 1 to 6; $R^9$ represents a monovalent hydrocarbon group having 1 to 20 carbon atoms, a monovalent heteroatom-containing group comprising —O—, —CO—, —COO—, —SO$_2$O—, —NR$^b$SO$_2$—, —NR$^b$CO— or a combination thereof between two carbon atoms in the monovalent hydrocarbon group, or a group obtained by substituting a part or all of hydrogen atoms included in any one of the monovalent hydrocarbon group or the monovalent heteroatom-containing group with a hydroxy group, a halogen atom or a combination thereof; and optionally, in a case where n is 2 or greater, two or more $R^9$s among a plurality of $R^9$s taken together represent a ring structure having 3 to 10 ring atoms, a heteroring structure comprising —O—, —CO—, —COO—, —SO$_2$O—, —NR$^b$SO$_2$—, —NR$^b$CO— or a combination thereof between two carbon atoms in the ring structure, or a group obtained by substituting a part or all of hydrogen atoms included in any one of the ring structure or the heteroring structure with a hydroxy group, a halogen atom or a combination thereof, wherein $R^b$ represents a hydrogen atom or a monovalent hydrocarbon group having 1 to 10 carbon atoms; $R^{10}$ represents a hydrogen atom or a monovalent hydrocarbon group having 1 to 10 carbon atoms; $R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms together with the nitrogen atom to which $R^{13}$ and $R^{14}$ bond.

According to further aspect of the present invention, a production method includes reacting a compound represented by a formula (i-a) and an amine compound represented by a formula (i-b) to produce a compound represented by a formula (1).

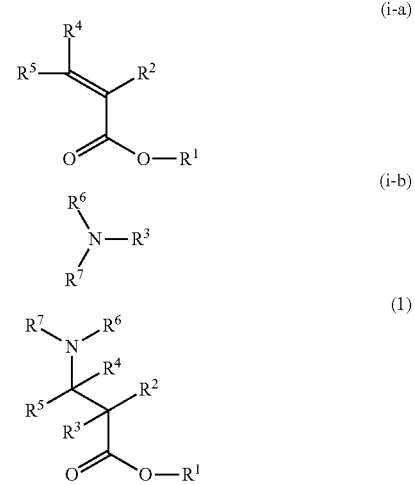

In the formulae (i-a), (i-b) and (1), $R^1$ represents a hydrocarbon group comprising a monovalent alicyclic structure having 3 to 30 carbon atoms, a heteroatom-containing group comprising —O—, —CO—, —COO—, —SO$_2$O—, —NR$^a$SO$_2$—, —NR$^a$CO— or a combination thereof between two carbon atoms in the hydrocarbon group, an aromatic hydrocarbon group having 6 to 30 carbon atoms, or a group obtained by substituting a part or all of hydrogen atoms included in any one of the hydrocarbon group, the heteroatom-containing group or the aromatic hydrocarbon group with a hydroxy group, a halogen atom or a combination thereof, wherein $R^a$ represents a hydrogen atom or a hydrocarbon group having 1 to 10 carbon atoms; $R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms; $R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms together with the nitrogen atom to which $R^6$ and $R^7$ bond.

According to further aspect of the present invention, a production method includes reacting a compound represented by a formula (ii-a) and an amine compound represented by a formula (ii-b) to produce a compound represented by a formula (2).

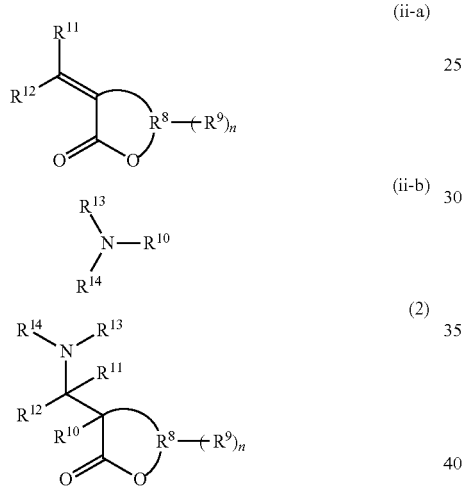

In the formulae (ii-a), (ii-b) and (2), $R^8$ is represents a monocyclic heterocyclic group having a valency of (n+2) and having 5 to 8 ring atoms together with the ester group to which $R^8$ bonds and with the carbon atom to which $R^{10}$ bonds; n is an integer of 1 to 6; $R^9$ represents a monovalent hydrocarbon group having 1 to 20 carbon atoms, a monovalent heteroatom-containing group comprising —O—, —CO—, —COO—, —SO$_2$O—, —NR$^b$SO$_2$, —NR$^b$CO— or a combination thereof between two carbon atoms in the monovalent hydrocarbon group, or a group obtained by substituting a part or all of hydrogen atoms included in any one of the monovalent hydrocarbon group or the monovalent heteroatom-containing group with a hydroxy group, a halogen atom or a combination thereof; and optionally, in a case where n is 2 or greater, two or more $R^9$s among a plurality of $R^9$s taken together represent a ring structure having 3 to 10 ring atoms, a heteroring structure comprising —O—, —CO—, —COO—, —SO$_2$O—, —NR$^b$SO$_2$, —NR$^b$CO— or a combination thereof between two carbon atoms in the ring structure, or a group obtained by substituting a part or all of hydrogen atoms included in any one of the ring structure or the heteroring structure with a hydroxy group, a halogen atom or a combination thereof; wherein $R^b$ represents a hydrogen atom or a monovalent hydrocarbon group having 1 to 10 carbon atoms; $R^{10}$ represents a hydrogen atom or a monovalent hydrocarbon group having 1 to 10 carbon atoms; $R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms together with the nitrogen atom to which $R^{13}$ and $R^{14}$ bond.

DESCRIPTION OF THE EMBODIMENTS

According to an embodiment of the invention,
an acid diffusion control agent contains at least one selected from the group consisting of a compound represented by the following formula (1) and a compound represented by the following formula (2):

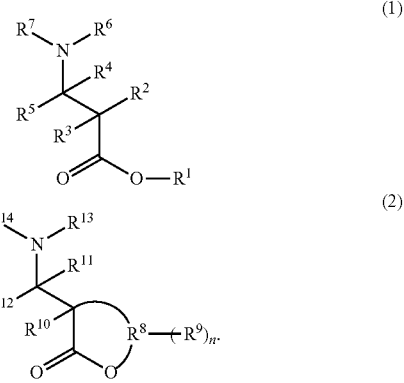

In the formula (1),
$R^1$ represents a hydrocarbon group having a monovalent alicyclic structure having 3 to 30 carbon atoms, a group that includes at least one selected from the group consisting of —O—, —CO—, —COO—, —SO$_2$O—, —NR$^a$SO$_2$— and —NR$^a$CO— between two carbon atoms in the hydrocarbon group, or an aromatic hydrocarbon group having 6 to 30 carbon atoms, or a group obtained by substituting a part or all of hydrogen atoms included in any one of these groups with at least one selected from the group consisting of a hydroxy group and a halogen atom, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms through binding with each other together with the nitrogen atom to which $R^6$ and $R^7$ bond.

In the formula (2),
$R^8$ is a group that taken together represents a monocyclic heterocyclic group having a valency of (n+2) and having 5 to 8 ring atoms together with the ester group and the carbon atom to which $R^{10}$ bond; and n is an integer of 1 to 6;

$R^9$ represents a monovalent hydrocarbon group having 1 to 20 carbon atoms in a case where n is an integer of 1 to 6, or $R^9$s represent a ring structure having 3 to 10 ring atoms obtained by binding two or more among a plurality of $R^9$s in a case where n is 2 or greater, or a group that includes at least one selected from the group consisting of —O—, —CO—, —COO—, —SO$_2$O—, —NR$^b$SO$_2$ and —NR$^b$CO— between two carbon atoms in the monovalent hydrocarbon group or the ring structure, or a group obtained by substituting a part or all of hydrogen atoms included in any one of these groups or ring structures with at least one selected from the group consisting of a hydroxy group and a halogen atom, wherein $R^b$ represents a hydrogen atom or a monovalent hydrocarbon group having 1 to 10 carbon atoms;

$R^{10}$ represents a hydrogen atom or a monovalent hydrocarbon group having 1 to 10 carbon atoms;

$R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms through binding with each other together with the nitrogen atom to which $R^{13}$ and $R^{14}$ bond.

The radiation-sensitive resin composition according to another embodiment of the present invention contains:
a polymer having an acid-labile group;
an acid generator; and
the acid diffusion control agent of the aforementioned embodiment.

The resist pattern-forming method according to still another embodiment of the present invention includes the steps of:
providing a resist film using the radiation-sensitive resin composition according to the another embodiment of the present invention;
exposing the resist film; and
developing the resist film exposed.

The compound according to still other embodiment of the present invention is represented by the following formula (1):

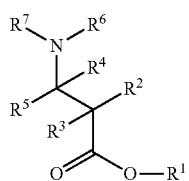

wherein, in the formula (1), $R^1$ represents a hydrocarbon group having a monovalent alicyclic structure having 3 to 30 carbon atoms, a group that includes at least one selected from the group consisting of —O—, —CO—, —COO—, —SO$_2$O—, —NR$^a$SO$_2$— and —NR$^a$CO— between two carbon atoms in the hydrocarbon group, or an aromatic hydrocarbon group having 6 to 30 carbon atoms, or a group obtained by substituting a part or all of hydrogen atoms included in any one of these groups with at least one selected from the group consisting of a hydroxy group and a halogen atom, wherein $R^a$ represents a hydrogen atom or a hydrocarbon group having 1 to 10 carbon atoms.

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms through binding with each other together with the nitrogen atom to which $R^6$ and $R^7$ bond.

Furthermore, another compound according to a yet another embodiment of the present invention is represented by the following formula (2):

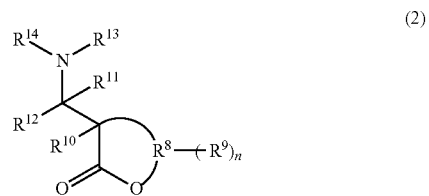

wherein, in the formula (2), $R^8$ is a group that taken together represents a monocyclic heterocyclic group having a valency of (n+2) and having 5 to 8 ring atoms together with the ester group and the carbon atom to which $R^{10}$ bond; and n is an integer of 1 to 6;

$R^9$ represents a monovalent hydrocarbon group having 1 to 20 carbon atoms in a case where n is an integer of 1 to 6, or a ring structure having 3 to 10 ring atoms obtained by binding two or more among a plurality of $R^9$s in a case where n is 2 or greater, or a group that includes at least one selected from the group consisting of —O—, —CO—, —COO—, —SO$_2$O—, —NR$^b$SO$_2$ and —NR$^b$CO— between two carbon atoms in the monovalent hydrocarbon group or the ring structure, or a group obtained by substituting a part or all of hydrogen atoms included in any one of these groups or ring structures with at least one selected from the group consisting of a hydroxy group and a halogen atom, wherein $R^b$ represents a hydrogen atom or a monovalent hydrocarbon group having 1 to 10 carbon atoms;

$R^{10}$ represents a hydrogen atom or a monovalent hydrocarbon group having 1 to 10 carbon atoms;

$R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms through binding with each other together with the nitrogen atom to which $R^{13}$ and $R^{14}$ bond.

The production method of the compound according to other embodiment of the present invention is a production method of a compound represented by the following formula (1) including the step of:

reacting a compound represented by the following formula (i-a) and an amine compound represented by the following formula (i-b):

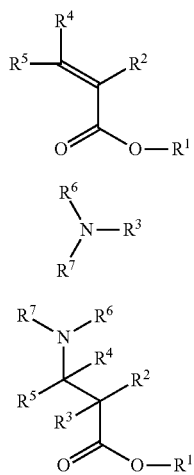

(i-a)

(i-b)

(1)

wherein, in the formulae (i-a), (i-b) and (1), $R^1$ represents a hydrocarbon group having a monovalent alicyclic structure having 3 to 30 carbon atoms, a group that includes at least one selected from the group consisting of —O—, —CO—, —COO—, —SO$_2$O—, —NR$^a$SO$_2$— and —NR$^a$CO— between two carbon atoms in the hydrocarbon group, or an aromatic hydrocarbon group having 6 to 30 carbon atoms, or a group obtained by substituting a part or all of hydrogen atoms included in any one of these groups with at least one selected from the group consisting of a hydroxy group and a halogen atom, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms through binding with each other together with the nitrogen atom to which $R^6$ and $R^7$ bond.

Another production method of the compound according to still other embodiment of the present invention is a production method of a compound represented by the following formula (2) including the step of:

reacting a compound represented by the following formula (ii-a) and an amine compound represented by the following formula (ii-b):

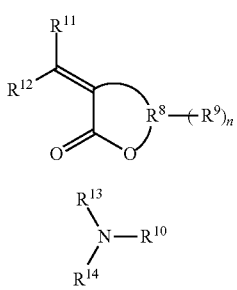

(ii-a)

(ii-b)

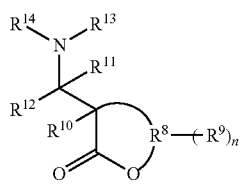

(2)

wherein, in the formulae (ii-a), (ii-b) and (2), $R^8$ is a group that taken together represents a monocyclic heterocyclic group having a valency of (n+2) and having 5 to 8 ring atoms together with the ester group and the carbon atom to which $R^{10}$ bond; and n is an integer of 1 to 6;

$R^9$ represents a monovalent hydrocarbon group having 1 to 20 carbon atoms in a case where n is an integer of 1 to 6, or a ring structure having 3 to 10 ring atoms obtained by binding two or more among a plurality of $R^9$s in a case where n is 2 or greater, or a group that includes at least one selected from the group consisting of —O—, —CO—, —COO—, —SO$_2$O—, —NR$^b$SO$_2$ and —NR$^b$CO— between two carbon atoms in the monovalent hydrocarbon group or the ring structure, or a group obtained by substituting a part or all of hydrogen atoms included in any one of these groups or ring structures with at least one selected from the group consisting of a hydroxy group and a halogen atom, wherein $R^b$ represents a hydrogen atom or a monovalent hydrocarbon group having 1 to 10 carbon atoms;

$R^{10}$ represents a hydrogen atom or a monovalent hydrocarbon group having 1 to 10 carbon atoms;

$R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms through binding with each other together with the nitrogen atom to which $R^{13}$ and $R^{14}$ bond.

The term "chain hydrocarbon group" as referred to herein means a hydrocarbon group constructed with only a chain structure, without including a ring structure. The term "hydrocarbon group having an alicyclic structure" as referred to means a hydrocarbon group that includes an alicyclic structure as a ring structure; however, it is not necessary to be constructed only with an alicyclic structure, and an aromatic ring structure or a chain structure may be included in part thereof. The term "aromatic hydrocarbon group" as referred to means a hydrocarbon group that includes only an aromatic ring structure as a ring structure; however, it is not necessary to be constructed only with an aromatic ring structure, and a chain structure may be included in part thereof.

According to the acid diffusion control agent, the radiation-sensitive resin composition containing the same, and the resist pattern-forming method in which the radiation-sensitive resin composition is used of the embodiments of the present invention, while exhibiting a great depth of focus, a resist pattern having small LWR, superior rectangularity of the cross-sectional shape, and a high resolution can be formed. In addition, the compound according to still other embodiment of the present invention can be suitably used as the acid diffusion control agent. According to the production method of the compound of other embodiments of the present invention, the compound can be conveniently produced. Therefore, these can be suitably used for pattern formation in manufacture of semiconductor devices in which further progress of miniaturization is expected in the future. The embodiments will now be described in detail.

Acid Diffusion Control Agent

The acid diffusion control agent (hereinafter, may be also referred to as "acid diffusion control agent (I)") includes at least one (hereinafter, may be also referred to as "compound (I)") selected from the group consisting of a compound represented by the above formula (1) (hereinafter, may be also referred to as "compound (1)") and a compound represented by the formula (2) (hereinafter, may be also referred to as "compound (2)"). Since the acid diffusion control agent (I) includes the compound (I), a radiation-sensitive resin composition containing the same is favorable in LWR performance, resolution, rectangularity of the cross-sectional shape and the depth of focus. Although not necessarily clarified, the reason for achieving the effects described above due to the acid diffusion control agent (I) containing the compound (I) is presumed, for example, as set forth below.

The compound (I) has a specific structure including: an ester group together with a nitrogen atom capable of interacting with an acid; a ring structure in the vicinity of the ester group or a ring structure that includes an ester group; and further, a specific group that is a hydrocarbon group or a group derived therefrom in the vicinity of the ester group. Since the compound (I) thus includes a polar ester group, a bulky ring structure and a specific group that achieves a steric effect in the vicinity with one another, it is believed that a synergistic effect thereby is exhibited, and as compared with conventional nitrogen atom-containing compounds, sublimability is reduced and superior heat resistance is attained while an affinity of the compound (I) to the polymer and the like constituting the resist film is increased. Thus, diffusion and uneven distribution of the compound (I) in the resist film is appropriately suppressed. As a result, the radiation-sensitive resin composition containing the compound (I) has favorable LWR performance, resolution, rectangularity of the cross-sectional shape and depth of focus.

In addition, due to having the specific structure described above, the compound (I) can be conveniently synthesized from an acrylic acid ester compound or an α-methylenelactone compound, and an amine compound; therefore, raw materials are readily available, and advantages in terms of the production cost can be also achieved.

Hereinafter, the compound (1) and the compound (2) will be explained in this order.

Compound (1)

The compound (1) is represented by the following formula (1):

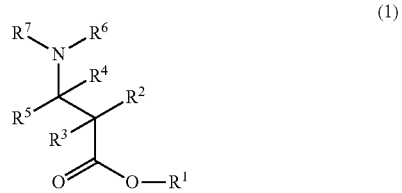

In the above formula (1), $R^1$ represents a hydrocarbon group having a monovalent alicyclic structure having 3 to 30 carbon atoms, a group that includes at least one selected from the group consisting of —O—, —CO—, —COO—, —SO$_2$O—, —NR$^a$SO$_2$— and —NR$^a$CO— between two carbon atoms in the hydrocarbon group, or an aromatic hydrocarbon group having 6 to 30 carbon atoms, or a group obtained by substituting a part or all of hydrogen atoms included in any one of these groups with at least one selected from the group consisting of a hydroxy group and a halogen atom, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms through binding with each other together with the nitrogen atom to which $R^6$ and $R^7$ bond.

The hydrocarbon group having a monovalent alicyclic structure having 3 to 30 carbon atoms represented by $R^1$ is exemplified by an acid-nonlabile hydrocarbon group having an alicyclic structure, an acid-labile hydrocarbon group having an alicyclic structure, and the like. The "acid-labile hydrocarbon group having an alicyclic structure" as referred to means a hydrocarbon group which has an alicyclic structure that substitutes a hydrogen atom of a carboxy group, a hydroxy group, etc., and which is dissociated by an action of an acid.

Examples of the acid-nonlabile hydrocarbon group having an alicyclic structure include:

monocyclic cycloalkyl groups such as a cyclopropyl group, a cyclobutyl group, a cyclopentyl group, a 1-i-propylcyclopentan-1-yl group, a cyclohexyl group, a cycloheptyl group, a cyclooctyl group, a cyclodecyl group, a 2-methyladamantan-2-yl group and a 2-i-propyladamantan-2-yl group;

polycyclic cycloalkyl groups such as a norbornyl group, an adamantyl group, a tricyclodecyl group and a tetracyclododecyl group;

monocyclic cycloalkenyl groups such as a cyclopentenyl group and a cyclohexenyl group;

polycyclic cycloalkenyl groups such as a norbornenyl group and a tricyclodecenyl group; and the like.

Of these, the acid-nonlabile hydrocarbon group having an alicyclic structure is preferably a monocyclic cycloalkyl group or a polycyclic cycloalkyl group, more preferably a polycyclic cycloalkyl group, still more preferably a group having an adamantane ring or a group having a tricyclodecane ring, and particularly preferably a 1-adamantyl group or a 8-tricyclodecyl group.

The acid-labile hydrocarbon group having an alicyclic structure is exemplified by a group that provides a tertiary carbon atom at the binding site, and the like. Examples of the acid-labile hydrocarbon group having an alicyclic structure include:

alkyl group-substituted monocyclic cycloalkyl groups such as a 1-methyl-1-cyclopentyl group, a 1-ethyl-1-cyclopentyl group, a 1-i-propyl-1-cyclopentyl group and a 1-methyl-1-cyclohexyl group;

alkyl group-substituted polycyclic cycloalkyl groups such as a 2-methyl-2-adamantyl group, a 2-ethyl-2-adamantyl group, a 2-i-isopropyl-2-adamantyl group and a 2-methyl-2-norbornyl group;

cycloalkyl group-substituted alkyl groups such as a 2-cyclopentyl-2-propyl group, a 2-cyclohexyl-2-propyl group, a 2-norbornyl-2-propyl group and a 2-adamantyl-2-propyl group; and the like.

Of these, the acid-labile hydrocarbon group having an alicyclic structure is preferably an alkyl group-substituted monocyclic cycloalkyl group or an alkyl group-substituted polycyclic cycloalkyl group, more preferably a 1-alkyl-1-monocycliccycloalkyl group or a 2-alkyl-2-polycyclic cycloalkyl group, still more preferably a 1-alkyl-1-cyclopentyl group or a 2-alkyl-2-adamantyl group, and particularly preferably a 1-i-propyl-1-cyclopentyl group, a 2-ethyl-2-adamantyl group or a 2-i-propyl-2-adamantyl group.

When $R^1$ represents an acid-labile hydrocarbon group having an alicyclic structure, the compound (1) is dissociated by an action of an acid generated from the acid generator at a light-exposed site to yield a carboxy group. As a result, diffusion of the compound (1) in the resist film can be more suitably controlled. In addition, since $R^1$ is dissociated by an action of an acid, an affinity to a developer solution is altered; therefore, contrast of dissolution of the radiation-sensitive resin composition containing the acid diffusion control agent is improved. Specifically, at a light-exposed site, solubility in alkaline developer solutions is improved, whereas a dissolution inhibitory effect is improved in organic solvent developer solutions.

Examples of the group that includes —O— between two carbon atoms in the hydrocarbon group having an alicyclic structure include:

groups having an oxacycloalkane structure such as an oxacyclopentyl group and an oxacyclohexyl group;

groups having a cyclic acetal ring (including a cyclic ketal ring) such as a 1,3-dioxa-2,2-dimethylcyclopentan-5-ylmethyl group and a 1,3-dioxacyclopentan-5-ylmethyl group;

groups having an oxacycloalkane structure and a cyclic acetal ring such as a 7-(1,3-dioxa-2,2-dimethylcyclopentan-4-yl)-3,3-dimethyl-2,4,8-trioxabicyclo[3,3,0]octan-6-yl group and a 7-(1,3-dioxa-spiro[adamantane-2,2']cyclopentan-4-yl)-spiro[adamantane-3,3']-2,4,8-trioxabicyclo[3,3,0]octan-6-yl group; and the like.

Of these, groups having a cyclic acetal ring, and groups having an oxacycloalkane structure and a cyclic acetal ring are preferred, and a 1,3-dioxa-2,2-dimethylcyclopentan-5-ylmethyl group, a 7-(1,3-dioxa-2,2-dimethylcyclopentan-4-yl)-3,3-dimethyl-2,4,8-trioxabicyclo[3,3,0]octan-6-yl group and a 7-(1,3-dioxa-spiro[adamantane-2,2']cyclopentan-4-yl)-spiro[adamantane-3,3']-2,4,8-trioxabicyclo[3,3,0]octan-6-yl group are more preferred.

When $R^1$ represents a group having a cyclic acetal ring, the compound (1) yields two hydroxy groups by an action of an acid generated from the acid generator at a light-exposed site. As a result, diffusion of the compound (1) in the resist film can be more suitably controlled. In addition, owing to the dissociation by an action of the acid generated from the acid generator, an affinity to a developer solution is altered; therefore, contrast of dissolution is improved. Specifically, at a light-exposed site, solubility in alkaline developer solutions is improved, whereas a dissolution inhibitory effect is improved in organic solvent developer solutions.

Examples of the group that includes —CO— between two carbon atoms in the hydrocarbon group having an alicyclic structure include:

cyclic ketone groups such as an oxocyclopentyl group, an oxocyclohexyl group, an oxonorbornyl group, an oxoadamantyl group, a dioxocyclopentyl group, a dioxocyclohexyl group, a dioxonorbornyl group and a dioxoadamantyl group;

chain groups having a cyclic ketone group such as a norbornylcarbonylmethyl group and an adamantylcarbonylmethyl group; and the like.

Of these, chain groups having a cyclic ketone group are preferred, and a norbornylcarbonylmethyl group is more preferred.

Examples of the group that includes —COO— between two carbon atoms in the hydrocarbon group having an alicyclic structure include:

groups having a lactone structure such as a butyrolacton-yl group, a valerolacton-yl group, a caprolacton-yl group, a norbornanelacton-yl group and a 5-oxo-4-oxatricyclo[4.3.1.1$^{3,8}$]undecan-yl group;

ester group-containing chain groups having a group having a lactone structure such as lacton-yloxycarbonyl alkyl groups such as a norbornanelacton-yloxycarbonylmethyl group and a butyrolacton-yloxycarbonylmethyl group; and the like.

Of these, a norbornanelacton-yl group, and a norbornanelacton-yloxycarbonylmethyl group are preferred.

Examples of the group that includes —SO$_2$O— between two carbon atoms in the hydrocarbon group having an alicyclic structure include groups having a sultone structure such as a butyrosulton-yl group, a valerosulton-yl group and a norbornanesulton-yl group; and the like.

Of these, a norbornanesulton-yl group is preferred.

Examples of the group that includes —NR$^a$SO$_2$— between two carbon atoms in the hydrocarbon group having an alicyclic structure include groups having a sultam structure such as a butyrosultam-yl group, a valerosultam-yl group and a norbornanesultam-yl group; and the like.

Of these, a norbornanesultam-yl group is preferred.

Examples of the group that includes —NR$^a$CO— between two carbon atoms in the hydrocarbon group having an alicyclic structure include groups having a lactam structure such as a butyrolactam-yl group, a valerolactam-yl group, a caprolactam-yl group and a norbornanelactam-yl group; and the like.

Of these, a caprolactam-yl group and a norbornanelactam-yl group are preferred.

The hydrocarbon group having 1 to 10 carbon atoms represented by $R^a$ is exemplified by a chain hydrocarbon group having 1 to 10 carbon atoms, an alicyclic hydrocarbon group having 3 to 10 carbon atoms, an aromatic hydrocarbon group having 6 to 10 carbon atoms, and the like.

Examples of the chain hydrocarbon group having 1 to 10 carbon atoms include:

alkyl groups such as a methyl group, an ethyl group, a propyl group and a butyl group;

alkenyl groups such as an ethenyl group, a propenyl group and a butenyl group;

alkynyl groups such as an ethynyl group, a propynyl group and a butynyl group; and the like.

Examples of the alicyclic hydrocarbon group having 3 to 10 carbon atoms include:

cycloalkyl groups such as a cyclopropyl group, a cyclobutyl group, a cyclopentyl group, a cyclohexyl group, a norbornyl group, an adamantyl group and a tricyclodecyl group;

cycloalkenyl groups such as a cyclobutenyl group, a cyclopentenyl group, a cyclohexenyl group and a norbornenyl group; and the like.

Examples of the aromatic hydrocarbon group having 6 to 10 carbon atoms include:

aryl groups such as a phenyl group, a tolyl group, a xylyl group, a mesityl group and a naphthyl group;

aralkyl groups such as a benzyl group, a phenethyl group and a phenylpropyl group; and the like.

R<sup>a</sup> described above is preferably a hydrogen atom or a chain hydrocarbon group, more preferably a hydrogen atom or an alkyl group, still more preferably a hydrogen atom, a methyl group or an ethyl group and particularly preferably a hydrogen atom.

Examples of the aromatic hydrocarbon group having 6 to 30 carbon atoms represented by $R^1$ include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a phenylpropyl group and a naphthylmethyl group; and the like.

Examples of the group obtained by substituting a hydrogen atom included in any one of these groups described above with a hydroxy group include:

hydroxy group-substituted monocyclic cycloalkyl groups such as a hydroxycyclopentyl group, a hydroxycyclohexyl group, a dihydroxycyclopentyl group and a dihydroxycyclohexyl group;

hydroxy group-substituted polycyclic cycloalkyl groups such as a hydroxynorbornyl group, a hydroxyadamantyl group, a dihydroxynorbornyl group and a dihydroxyadamantyl group;

hydroxy group-substituted aryl groups such as a hydroxyphenyl group, a hydroxytolyl group, a hydroxynaphthyl group and a hydroxyanthryl group; and the like.

Of these, hydroxy group-substituted polycyclic cycloalkyl groups are preferred, a hydroxyadamantyl group is more preferred, and a 3-hydroxy-1-adamantyl group is still more preferred.

Examples of the halogen atom that substitutes the hydrogen atom included in these groups described above include a fluorine atom, a chlorine atom, a bromine atom, an iodine atom, and the like.

Examples of the group obtained by substituting a hydrogen atom included in any one of these groups described above with a halogen atom include:

halogen atom-substituted monocyclic cycloalkyl groups such as a halocyclopentyl group, a halocyclohexyl group, a dihalocyclopentyl group and a dihalocyclohexyl group;

halogen atom-substituted polycyclic cycloalkyl groups such as a halonorbornyl group, a haloadamantyl group, a dihalonorbornyl group and a dihaloadamantyl group;

halogen atom-substituted aryl groups such as a halophenyl group, a halotolyl group, a halonaphthyl group and a haloanthryl group; and the like.

Of these, halogen atom-substituted monocyclic cycloalkyl groups are preferred, and a perfluorocycloalkyl group is more preferred.

$R^1$ is preferably an acid-nonlabile monocyclic or polycyclic cycloalkyl group, an acid-labile cycloalkyl group, a cycloalkyl group substituted with a hydroxy group, or a group that includes —O—, —COO— and/or —SO$_2$O— between two carbon atoms in a cycloalkyl group, more preferably an acid-nonlabile monocyclic or polycyclic cycloalkyl group, an acid-labile cycloalkyl group, or a cycloalkyl group substituted with a hydroxy group, still more preferably an unsubstituted monocyclic cycloalkyl group, an unsubstituted polycyclic cycloalkyl group, a 1-alkyl-1-monocyclic cycloalkyl group, or a hydroxy-substituted polycyclic cycloalkyl group, and particularly preferably a cyclohexyl group, a 1-adamantyl group, a 3-hydroxy-1-adamantyl group or a 1-alkyl-1-cyclopentyl group.

The monovalent hydrocarbon group having 1 to 10 carbon atoms which may be represented by $R^2$ and $R^3$ is exemplified by groups similar to those exemplified in connection with the monovalent hydrocarbon group represented by $R^a$, and the like. Of these, chain hydrocarbon groups are preferred; an alkyl group is more preferred; a methyl group and an ethyl group are still more preferred; and a methyl group is particularly preferred.

As a combination of $R^2$ and $R^3$, a combination of a hydrogen atom and a monovalent hydrocarbon group is preferred in light of ease in synthesis of the compound (1).

The monovalent hydrocarbon group having 1 to 10 carbon atoms which may be represented by $R^4$ and $R^5$ is exemplified by groups similar to those exemplified in connection with the monovalent hydrocarbon group represented by $R^a$, and the like. Of these, chain hydrocarbon groups are preferred; alkyl groups are more preferred; a methyl group and an ethyl group are still more preferred; and a methyl group is particularly preferred.

$R^4$ and $R^5$ are preferably a hydrogen atom or an alkyl group, more preferably a hydrogen atom, a methyl group or an ethyl group, and still more preferably a hydrogen atom.

The monovalent hydrocarbon group having 1 to 10 carbon atoms which may be represented by $R^6$ and $R^7$ is exemplified by groups similar to those exemplified in connection with the monovalent hydrocarbon group represented by $R^a$, and the like. Of these, chain hydrocarbon groups are preferred; alkyl groups are more preferred; a methyl group, an ethyl group, a n-propyl group and an i-propyl group are still more preferred; and an ethyl group is particularly preferred.

Examples of the ring structure having 3 to 10 ring atoms taken together represented by $R^6$ and $R^7$ through binding with each other together with the nitrogen atom to which $R^6$ and $R^7$ bond include:

monocyclic azacycloalkane structures such as an azacyclopropane structure, an azacyclobutane structure, an azacyclopentane structure (pyrrolidine structure), an azacyclohexane structure (piperidine structure), an azacycloheptane structure, an azacyclooctane structure and an azacyclodecane structure;

polycyclic azacycloalkane structures such as an azabicyclo[2.2.1]heptane structure, an azabicyclo[2.2.2]octane structure and an azatricyclo[3.3.1.1$^{3,7}$]decane structure;

azaoxacycloalkane structures such as an azaoxacyclopropane structure and an azaoxacyclohexane structure (including a morpholine structure); and the like.

Of these, monocyclic azacycloalkane structures and azaoxacycloalkane structures are preferred; an azacyclopentane structure, an azacyclohexane structure and an azaoxacyclohexane structure are more preferred; and an azacyclohexane structure and a 1,4-azaoxacyclohexane structure (morpholine structure) are still more preferred.

The compound (1) is exemplified by compounds represented by the following formulae (i-1) to (i-20) (hereinafter, may be also referred to as "compounds (i-1) to (i-20)"), and the like.

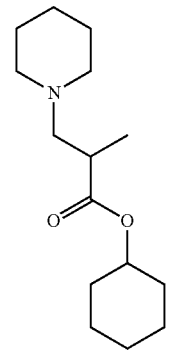

(i-1)

(i-2)
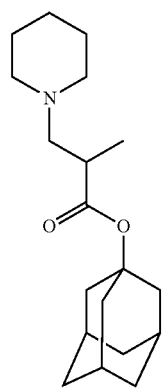
(i-3)
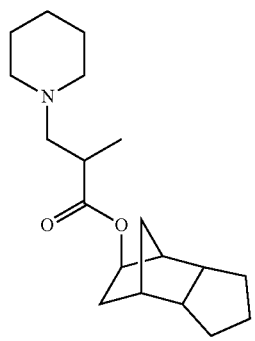
(i-4)
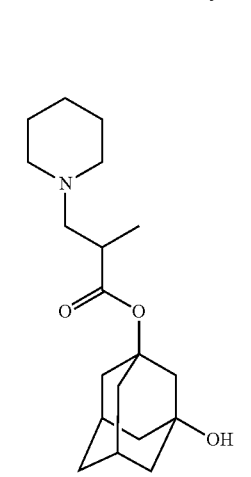
(i-5)
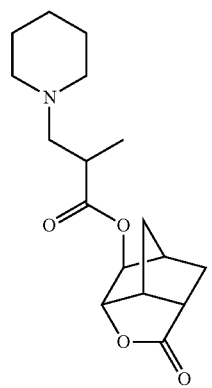
(i-6)
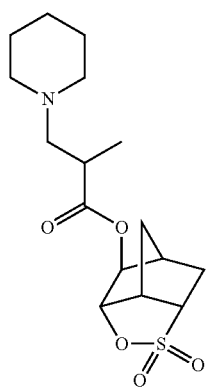
(i-7)
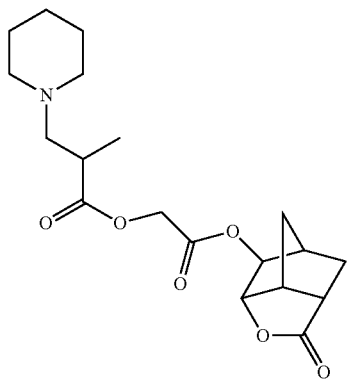
(i-8)
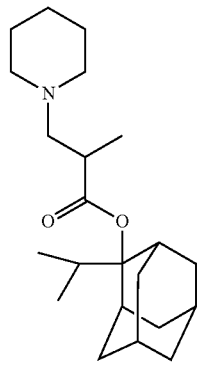
(i-9)
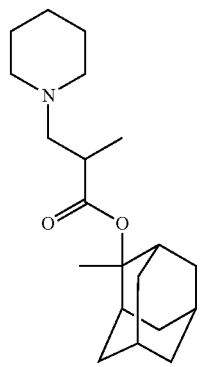

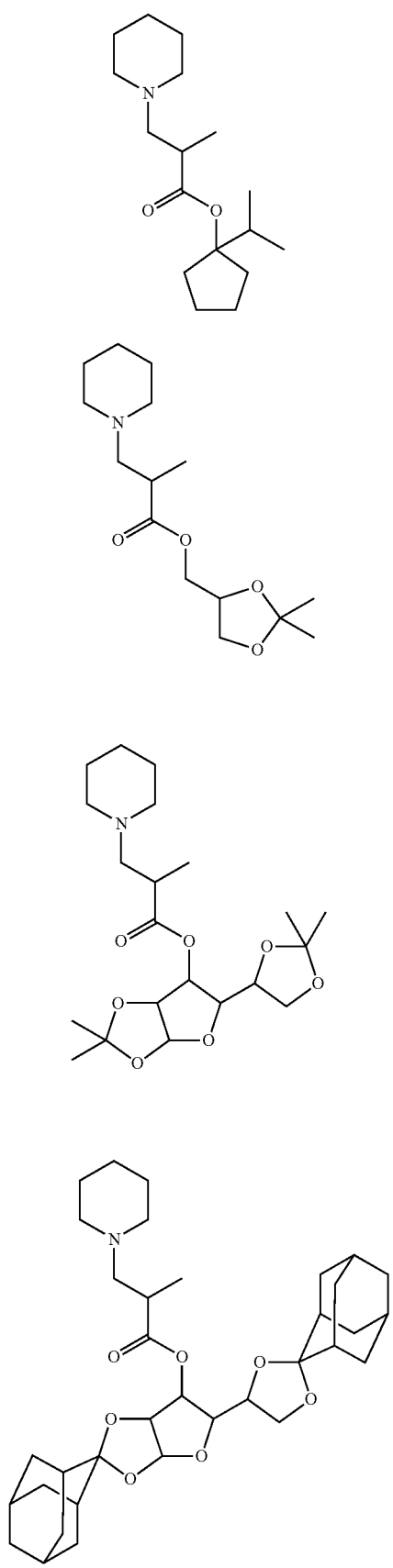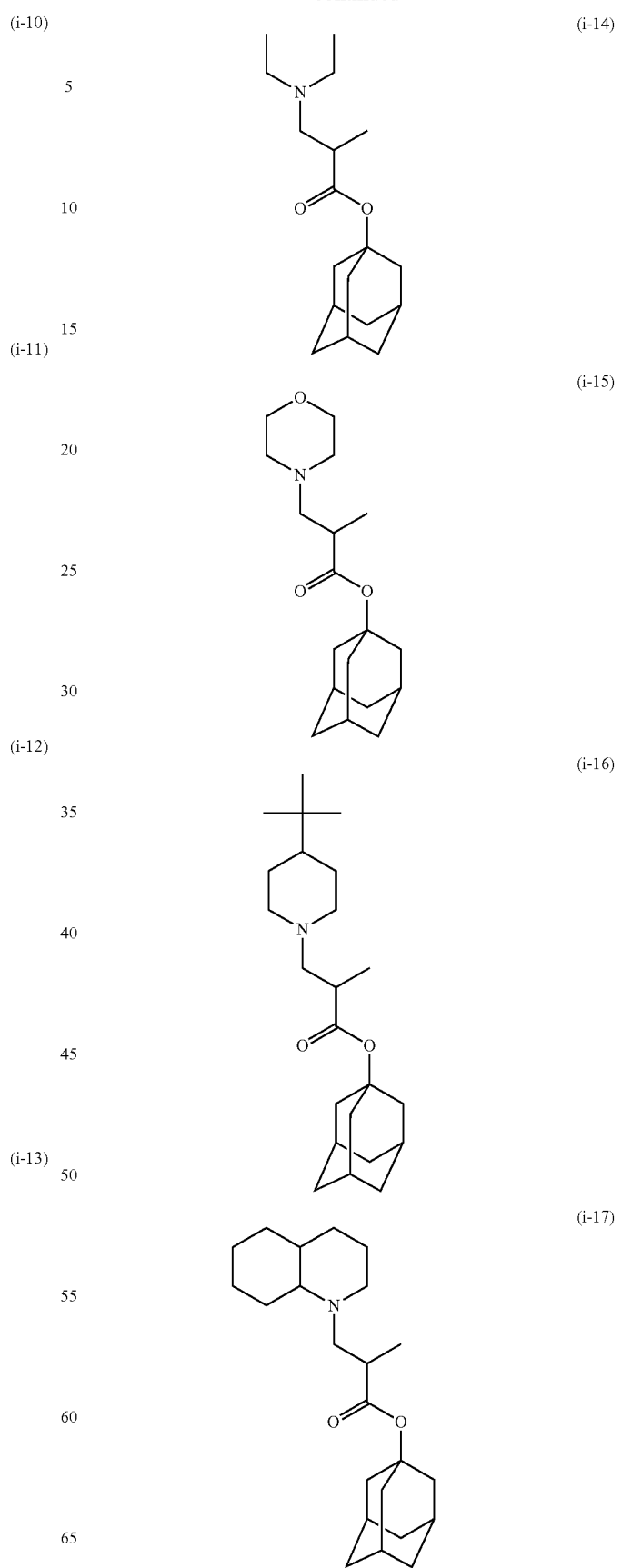

-continued

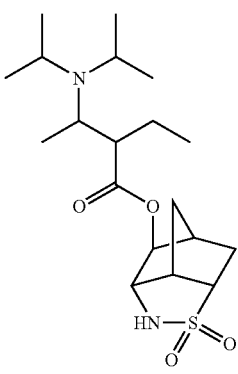
(i-18)

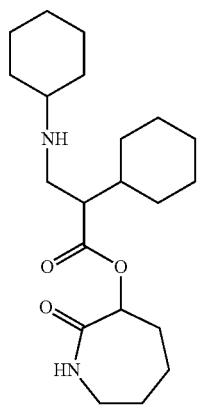
(i-19)

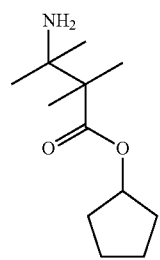
(i-20)

Of these, as the compound (1), the compounds (i-1) to (i-19) are preferred; the compounds (i-1) to (i-17) are more preferred; the compound (i-1), the compound (i-2), the compound (i-4), the compound (i-10) and the compound (i-17) are still more preferred.

Compound (2)

The compound (2) is represented by the following formula (2).

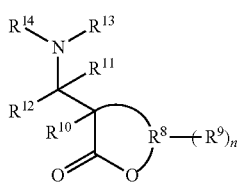
(2)

In the above formula (2), $R^8$ is a group that taken together represents a monocyclic heterocyclic group having a valency of (n+2) and having 5 to 8 ring atoms together with the ester group and the carbon atom to which $R^{10}$ bond; and n is an integer of 1 to 6;

$R^9$ represents a monovalent hydrocarbon group having 1 to 20 carbon atoms in a case where n is an integer of 1 to 6, or a ring structure having 3 to 10 ring atoms obtained by binding two or more among a plurality of $R^9$s in a case where n is 2 or greater, or a group that includes at least one selected from the group consisting of —O—, —CO—, —COO—, —SO$_2$O—, —NR$^b$SO$_2$— and —NR$^b$CO— between two carbon atoms in the monovalent hydrocarbon group or the ring structure, or a group obtained by substituting a part or all of hydrogen atoms included in any one of these groups or ring structures with at least one selected from the group consisting of a hydroxy group and a halogen atom, wherein $R^b$ represents a hydrogen atom or a monovalent hydrocarbon group having 1 to 10 carbon atoms;

$R^{10}$ represents a hydrogen atom or a monovalent hydrocarbon group having 1 to 10 carbon atoms;

$R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms through binding with each other together with the nitrogen atom to which $R^{13}$ and $R^{14}$ bond.

Examples of the monocyclic heterocyclic group having a valency of (n+2) and having 5 to 8 ring atoms represented by $R^8$ taken together with the ester group and the carbon atom to which $R^{10}$ bond include:

monocyclic lactones such as butyrolactone, valerolactone and caprolactone; groups obtained by removing (n+2) hydrogen atoms from a compound that includes a group having —O—, —S—, —NR— (wherein, R represents a hydrogen atom or a monovalent hydrocarbon group), —CO—, —CS— or a combination thereof between CH$_2$—CH$_2$ of any one of these lactones; and the like.

Of these, groups obtained by removing (n+2) hydrogen atoms from monocyclic lactone are preferred; groups obtained by removing (n+2) hydrogen atoms from butyrolactone, valerolactone or caprolactone are more preferred, and groups obtained by removing (n+2) hydrogen atoms from butyrolactone are still more preferred.

"n" is preferably 1 to 3, and more preferably 1 or 2.

The monovalent hydrocarbon group having 1 to 20 carbon atoms represented by $R^9$ in a case where n is an integer of 1 to 6 is exemplified by a chain hydrocarbon group having 1 to 20 carbon atoms, an alicyclic hydrocarbon group having 3 to 20 carbon atoms, an aromatic hydrocarbon group having 6 to 20 carbon atoms, and the like.

Examples of the chain hydrocarbon group having 1 to 20 carbon atoms include:

alkyl groups such as a methyl group, an ethyl group, a propyl group, a butyl group, a hexyl group, an octyl group, a decyl group, a dodecyl group, a tetradecyl group, an octadecyl group and an icosyl group;

alkenyl groups such as an ethenyl group, a propenyl group, a butenyl group, a hexenyl group, an octenyl group, a decenyl group, a dodecenyl group, a tetradecenyl group, an octadecenyl group and an icocenyl group;

alkynyl groups such as an ethynyl group, a propynyl group, a butynyl group, a hexynyl group, an octynyl group, a decynyl group, a dodecynyl group and a tetradecynyl group; and the like.

Examples of the alicyclic hydrocarbon group include:

cycloalkyl groups such as a cyclopropyl group, a cyclobutyl group, a cyclopentyl group, a cyclohexyl group, a norbornyl group, an adamantyl group, a tricyclodecyl group and a tetracyclododecyl group;

cycloalkenyl groups such as a cyclobutenyl group, a cyclopentenyl group, a cyclohexenyl group, a norbornenyl group, a tricyclodecenyl group and a tetracyclododecenyl group; and the like.

Examples of the aromatic hydrocarbon group include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a phenylpropyl group, a naphthylmethyl group and an anthrylmethyl group; and the like.

Examples of the ring structure having 3 to 10 ring atoms taken together represented by two or more among a plurality of $R^9$s through binding with each other in a case where n is 2 or greater include:

cycloalkane structures such as a cyclopropane structure, a cyclobutane structure, a cyclopentane structure, a cyclohexane structure, a norbornane structure and an adamantane structure;

oxacycloalkane structures such as an oxacyclobutane structure, an oxacyclopentane structure, an oxacyclohexane structure, an oxanorbornane structure and an oxaadamantane structure;

aromatic ring structures such as a benzene ring structure and a naphthalene ring structure; and the like.

To the ring structure may be bonded a substituent such as a hydroxy group, a halogen atom or a hydrocarbon group.

Also, the ring structure may be a spiro ring. In a case where two $R^9$s constituting the ring structure are bound to the same carbon atom, the two $R^9$s taken together represent a spiro ring.

Examples of the group that includes at least one selected from the group consisting of —O—, —COO—, —SO$_2$O—, —NR$^b$SO$_2$ and —NR$^b$CO— between two carbon atoms in the monovalent hydrocarbon group or the ring structure include the groups that include —O—, —COO—, —SO$_2$O—, —NR$^b$SO$_2$ or —NR$^b$CO— between two carbon atoms in the aforementioned chain hydrocarbon group, the aforementioned alicyclic hydrocarbon group, the aforementioned aromatic hydrocarbon group or the aforementioned ring structure, and the like.

The monovalent hydrocarbon group having 1 to 10 carbon atoms represented by $R^b$ is exemplified by groups similar to those exemplified in connection with the monovalent hydrocarbon group as $R^a$ described above, and the like. Of these, a hydrogen atom and a chain hydrocarbon group are preferred; a hydrogen atom and an alkyl group are more preferred; a hydrogen atom, a methyl group and an ethyl group are still more preferred; and a hydrogen atom is particularly preferred.

Examples of the group obtained by substituting a part or all of hydrogen atoms included in any one of these groups or ring structures with at least one selected from the group consisting of a hydroxy group and a halogen atom include the groups obtained by substituting with a hydroxy group or a halogen atom, a part or all of hydrogen atoms included in the chain hydrocarbon groups described above, the alicyclic hydrocarbon groups described above, the aromatic hydrocarbon groups described above, the ring structures described above, the group that includes at least one selected from the group consisting of —O—, —COO—, —SO$_2$O—, —NR$^b$SO$_2$ and —NR$^b$CO— between two carbon atoms in any one of these groups or ring structures; and the like.

$R^9$ is preferably the ring structure described above, more preferably a cyclobutane structure, a cyclopentane structure or a cyclohexane structure, still more preferably a group that includes at least one selected from the group consisting of —O—, —CO—, —COO—, —SO$_2$O—, —NR$^b$SO$_2$ and —NR$^b$CO— between two carbon atoms in any one of these ring structures, a group obtained by substituting a part or all of hydrogen atoms included in any one of these ring structures with at least one selected from the group consisting of a hydroxy group and a halogen atom, particularly preferably a group that includes —O— between two carbon atoms in any one of these ring structures, a group obtained by substituting a part of hydrogen atoms included in any one of these ring structures with a hydroxy group, and even more particularly preferably an oxacyclopentane structure, or a hydroxy-containing cyclohexane structure.

The monovalent hydrocarbon group having 1 to 10 carbon atoms represented by $R^{10}$ is exemplified by groups similar to those exemplified in connection with the monovalent hydrocarbon group as $R^a$ described above, and the like. Of these, a hydrogen atom and chain hydrocarbon groups are preferred; a hydrogen atom and alkyl groups are more preferred; a hydrogen atom, a methyl group and an ethyl group are still more preferred; and a hydrogen atom is particularly preferred.

$R^{10}$ is preferably a hydrogen atom or a chain hydrocarbon group, more preferably a hydrogen atom or an alkyl group, still more preferably a hydrogen atom, a methyl group or an ethyl group, and particularly preferably a hydrogen atom.

The monovalent hydrocarbon group having 1 to 10 carbon atoms represented by $R^{11}$ and $R^{12}$ is exemplified by groups similar to those exemplified in connection with the monovalent hydrocarbon group as $R^a$ described above, and the like. Of these, a hydrogen atom and chain hydrocarbon groups are preferred; a hydrogen atom and alkyl groups are more preferred; a hydrogen atom, a methyl group and an ethyl group are still more preferred; and a hydrogen atom is particularly preferred.

$R^{11}$ and $R^{12}$ are preferably a hydrogen atom or a chain hydrocarbon group, more preferably a hydrogen atom or an alkyl group, still more preferably a hydrogen atom, a methyl group or an ethyl group, and particularly preferably a hydrogen atom.

The monovalent hydrocarbon group having 1 to 10 carbon atoms represented by $R^{13}$ and $R^{14}$ is exemplified by groups similar to those exemplified as the monovalent hydrocarbon group represented by $R^a$, and the like. Of these, chain hydrocarbon groups are preferred; alkyl groups are more preferred; a methyl group, an ethyl group, a n-propyl group and an i-propyl group are still more preferred; and an i-propyl group is particularly preferred.

The ring structure having 3 to 10 ring atoms taken together represented by $R^{13}$ and $R^{14}$ through binding with each other together with the nitrogen atom to which $R^{13}$ and $R^{14}$ bond is exemplified by those similar to the ring structures exemplified as the ring structure represented by $R^6$ and $R^7$ through binding with each other together with the nitrogen atom to which $R^6$ and $R^7$ bond, and the like.

Of these, monocyclic azacycloalkane structures and azaoxacycloalkane structures are preferred; an azacyclopentane structure, an azacyclohexane structure and an azaoxacyclohexane structure are more preferred; and an azacyclohexane structure and a 1,4-azaoxacyclohexane structure (morpholine structure) are still more preferred.

The compound (2) is exemplified by compounds represented by the following formulae (ii-1) to (ii-13) (hereinafter, may be also referred to as "compounds (ii-1) to (ii-13)"), and the like.
(ii-1)
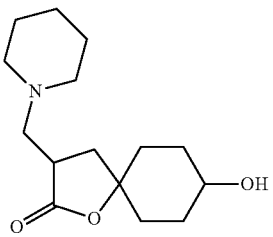
(ii-2)
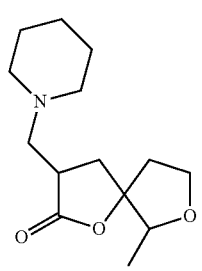
(ii-3)
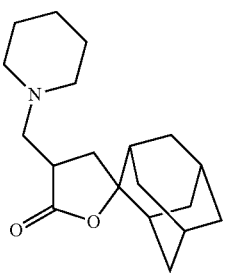
(ii-4)
(ii-5)
(ii-6)
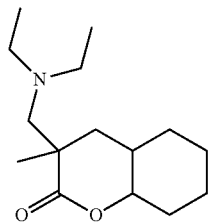
(ii-7)
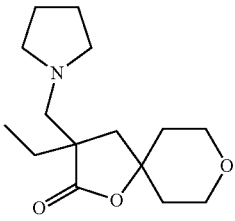
(ii-8)
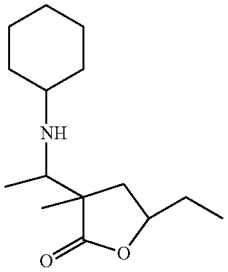
(ii-9)
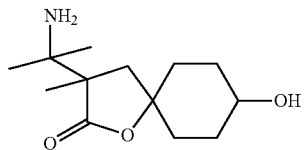
(ii-10)
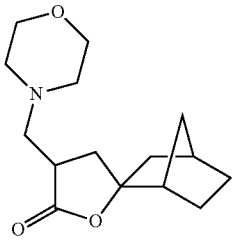
(ii-11)
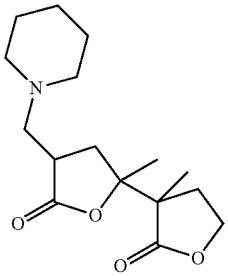

-continued (ii-12)

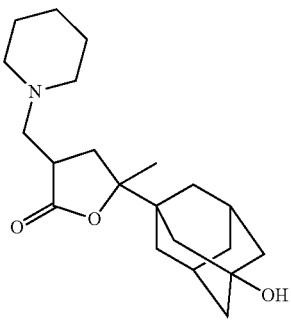

(ii-13)

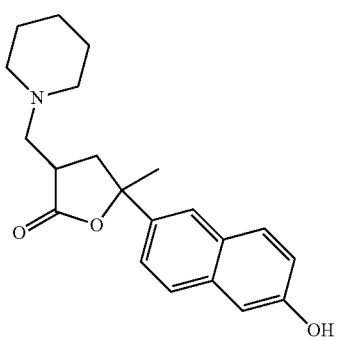

Of these, the compound (2) is preferably the compound (ii-1) to the compound (ii-4), and more preferably the compound (ii-1) and the compound (ii-2).

The compounds (1) and (2) may be synthesized according to, for example, the following reaction scheme. By this method, the compound (I) can be conveniently obtained.

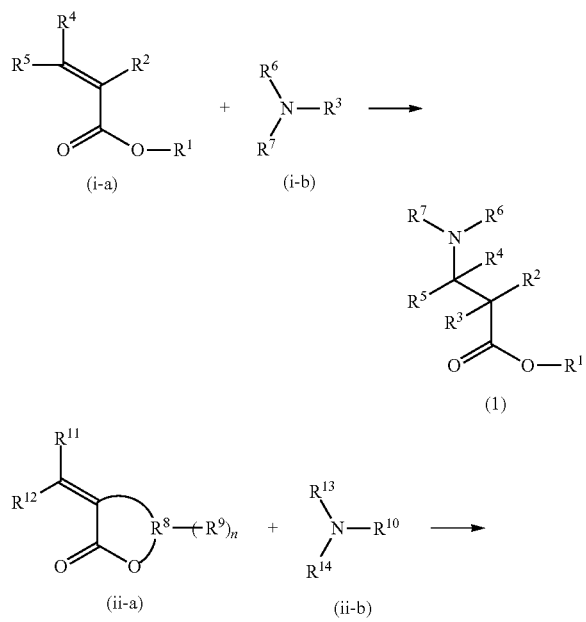

-continued

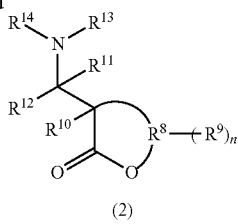

(2)

In the above reaction scheme, $R^1$ represents a hydrocarbon group having a monovalent alicyclic structure having 3 to 30 carbon atoms, a group that includes at least one selected from the group consisting of —O—, —CO—, —COO—, —SO$_2$O—, —NR$^a$SO$_2$— and —NR$^a$CO— between two carbon atoms in the hydrocarbon group, or an aromatic hydrocarbon group having 6 to 30 carbon atoms, or a group obtained by substituting a part or all of hydrogen atoms included in any one of these groups with at least one selected from the group consisting of a hydroxy group and a halogen atom, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms through binding with each other together with the nitrogen atom to which $R^6$ and $R^7$ bond.

$R^8$ is a group that taken together represents a monocyclic heterocyclic group having a valency of (n+2) and having 5 to 8 ring atoms together with the ester group and the carbon atom to which $R^{10}$ bond; and n is an integer of 1 to 6;

$R^9$ represents a monovalent hydrocarbon group having 1 to 20 carbon atoms in a case where n is an integer of 1 to 6, or a ring structure having 3 to 10 ring atoms obtained by binding two or more among a plurality of $R^9$s in a case where n is 2 or greater, or a group that includes at least one selected from the group consisting of —O—, —CO—, —COO—, —SO$_2$O—, —NR$^b$SO$_2$ and —NR$^b$CO— between two carbon atoms in the monovalent hydrocarbon group or the ring structure, or a group obtained by substituting a part or all of hydrogen atoms included in any one of these groups or ring structures with at least one selected from the group consisting of a hydroxy group and a halogen atom, wherein $R^b$ represents a hydrogen atom or a monovalent hydrocarbon group having 1 to 10 carbon atoms;

$R^{10}$ represents a hydrogen atom or a monovalent hydrocarbon group having 1 to 10 carbon atoms;

$R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms through binding with each other together with the nitrogen atom to which $R^{13}$ and $R^{14}$ bond.

The compound represented by the above formula (1) or (2) is obtained by reacting the acrylic acid ester compound represented by the above formula (i-a) or the α-methylenelactone compound represented by the formula (ii-a), with the amine compound represented by the above formula (i-b) or (ii-b) in a solvent such as toluene, in the presence of a base such as piperidine.

In light of ease in synthesis of the compounds represented by the above formula (1) and formula (2), $R^3$ and $R^{10}$ described above are preferably a hydrogen atom. Due to the group being a hydrogen atom, the reaction of the above scheme can more readily proceed, and consequently, the compounds can be obtained with a higher yield.

Thus, the compound (I) can be conveniently synthesized from an acrylic acid ester compound or an α-methylenelactone compound, and an amine compound; therefore, raw materials are readily available, and advantages in terms of the production cost can be also achieved.

Radiation-Sensitive Resin Composition

The radiation-sensitive resin composition contains a polymer having an acid-labile group (hereinafter, may be also referred to as "(A) polymer" or "polymer (A)"), an acid generator (hereinafter, may be also referred to as "(B) acid generator" or "acid generator (B)") and the acid diffusion control agent (hereinafter, may be also referred to as "(C) acid diffusion control agent" or "acid diffusion control agent (C)"). In addition to these components, the radiation-sensitive resin composition may further contain as favorable component(s), (D) an acid diffusion control agent other than the acid diffusion control agent (C) (hereinafter, may be also referred to as "(D) other acid diffusion control agent" or "other acid diffusion control agent (D)"), (E) a fluorine atom-containing polymer and (F) a solvent, and may contain other optional component within a range not leading to impairment of the effects of the present invention. Each component will be explained below.

(A) Polymer

The polymer (A) has an acid-labile group. In addition to a structural unit that includes an acid-labile group (hereinafter, may be also referred to as "structural unit (I)"), it is preferred that the polymer (A) further has (II) a structural unit that includes at least one selected from the group consisting of a lactone structure, a cyclic carbonate structure and a sultone structure, and/or (III) a structural unit that includes a polar group, and the polymer (A) may further have other structural unit except for these structural units. The polymer (A) may have each one, or two or more types of each structural unit. Each structural unit will be explained below.

Structural Unit (I)

The structural unit (I) includes an acid-labile group. The "acid-labile group" means a group that substitutes a hydrogen atom of an acidic group such as a carboxy group or a hydroxy group, and is dissociated by an action of an acid.

Examples of the structural unit (I) include a structural unit (I-1) represented by the following formula (3); and the like.

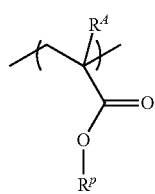

(3)

In the above formula (3), $R^A$ represents a hydrogen atom, a fluorine atom, a methyl group or a trifluoromethyl group; $R^P$ represents a monovalent acid-labile group represented by the following formula (p).

(p)

In the above formula (p), $R^{p1}$, $R^{p2}$ and $R^{p3}$ each independently represent an alkyl group having 1 to 4 carbon atoms or a cycloalkyl group having 4 to 20 carbon atoms, wherein, $R^{p2}$ and $R^{p3}$ optionally taken together represent a cycloalkanediyl group having 4 to 20 carbon atoms through binding with each other together with the carbon atom to which $R^{p2}$ and $R^{p3}$ bond.

It is preferred that the structural unit (I-1) is a structural unit represented by any one of the following formulae (3-1) to (3-4).

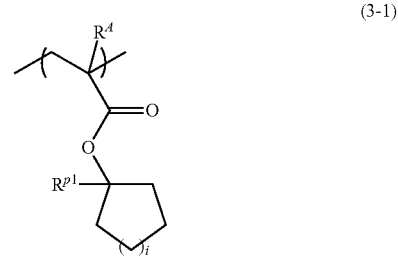

(3-1)

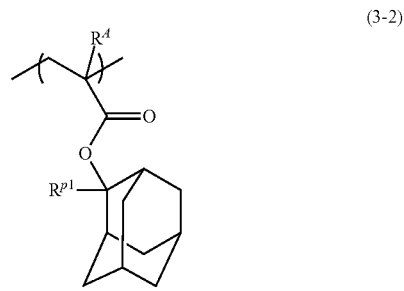

(3-2)

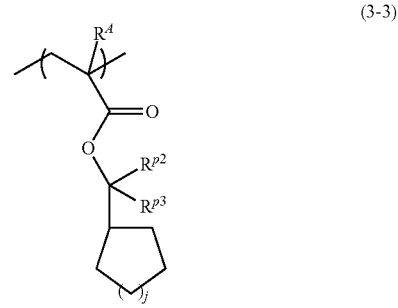

(3-3)

-continued

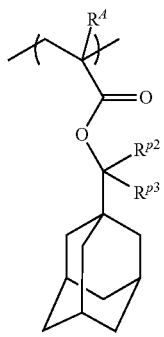
(3-4)

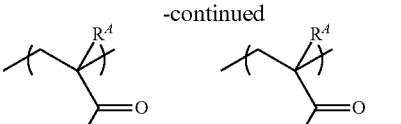

In the above formulae (3-1) to (3-4), $R^A$ is as defined in the above formula (3); $R^{p1}$, $R^{p2}$ and $R^{p3}$ are as defined in the above formula (p); and i and j are each independently an integer of 1 to 4.

Examples of the structural unit represented by the above formula (3) and the above formulae (3-1) to (3-4) include structural units represented by the following formulae, and the like.

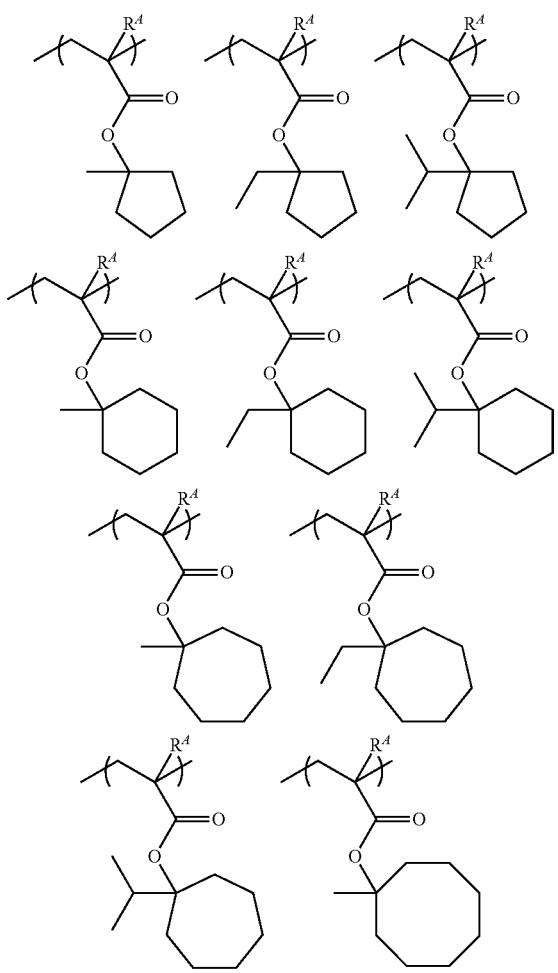

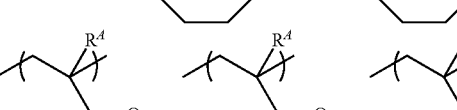

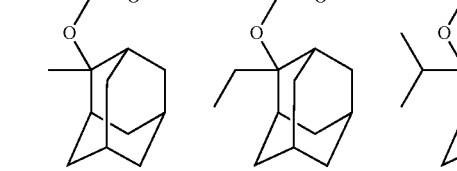

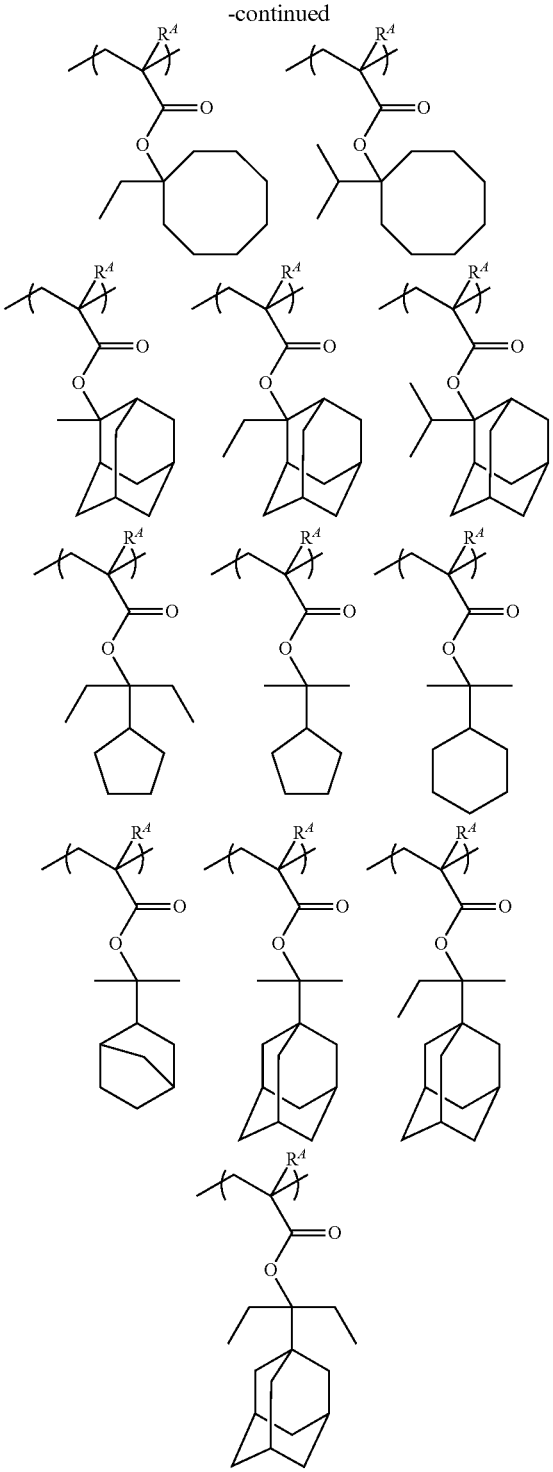

In the above formulae, $R^A$ is as defined in the above formula (3).

The structural unit (I) is preferably a structural unit represented by the above formula (3-1) or a structural unit represented by the formula (3-2), more preferably a structural unit derived from 1-alkyl-1-cyclopentyl (meth)acrylate or a structural unit derived from 2-alkyl-2-adamantyl (meth) acrylate, and still more preferably a structural unit derived from 1-ethyl-1-cyclopentyl (meth)acrylate or a structural unit derived from 2-ethyl-2-adamantyl (meth)acrylate.

The proportion of the structural unit (I) contained with respect to the total structural units constituting the polymer (A) is preferably 10 mol % to 100 mol %, more preferably 20 mol % to 80 mol %, and still more preferably 30 mol % to 70 mol %. When the proportion of the structural unit (I) contained falls within the above range, more favorable LWR performance, resolution, rectangularity of the cross-sectional shape and depth of focus of the radiation-sensitive resin composition may be attained. When the proportion of the structural unit (I) contained is less than the lower limit, pattern formability of the radiation-sensitive resin composition may be deteriorated.

Structural Unit (II)

The structural unit (II) includes at least one selected from the group consisting of a lactone structure, a cyclic carbonate structure and a sultone structure. When the polymer (A) further has the structural unit (II), solubility in developer solutions can be adjusted. In addition, the adhesiveness of the resist pattern formed from the radiation-sensitive resin composition to a substrate may be increased.

Examples of the structural unit (II) include structural units represented by the following formulae; and the like.

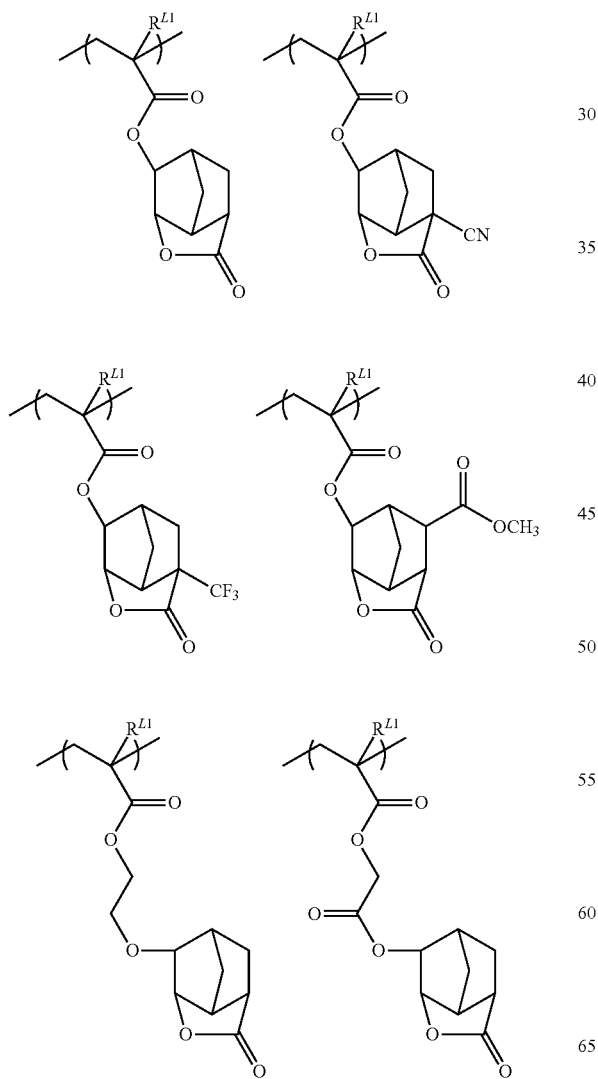

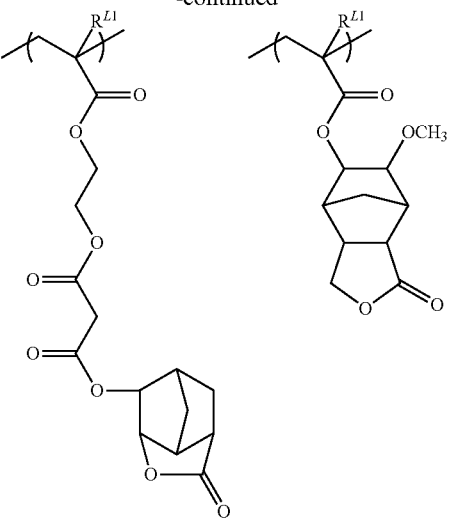

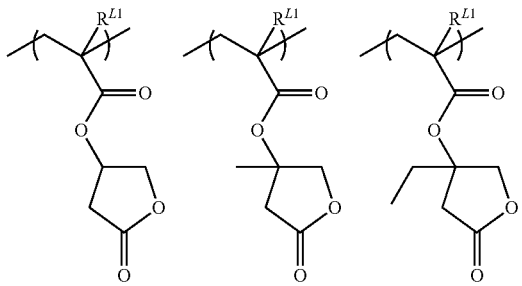

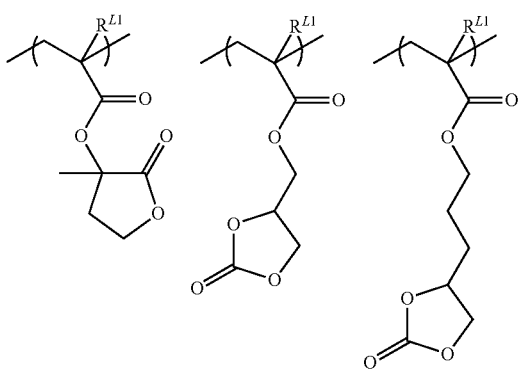

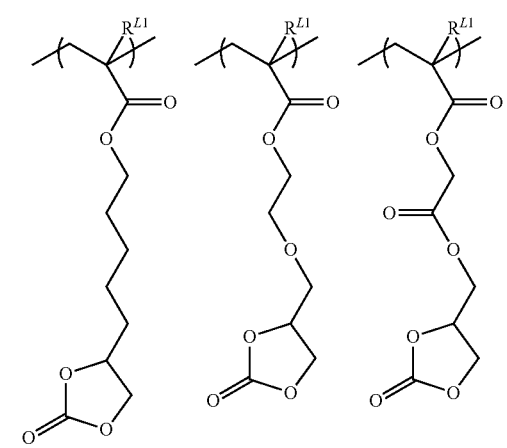

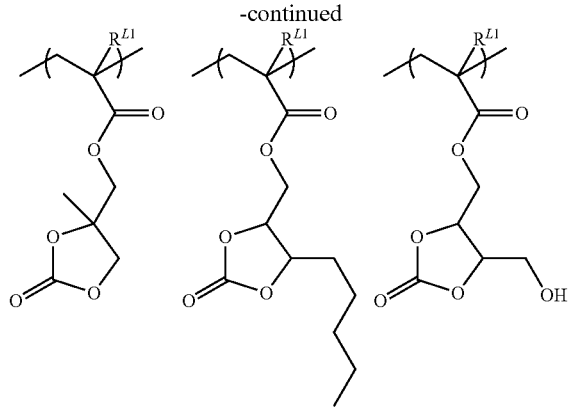
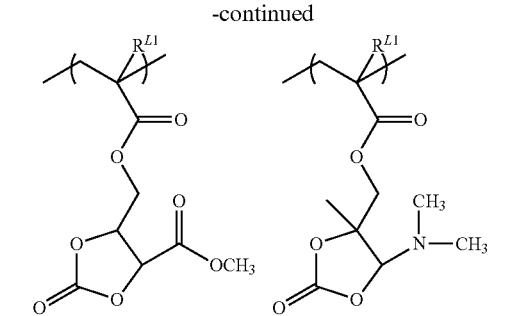
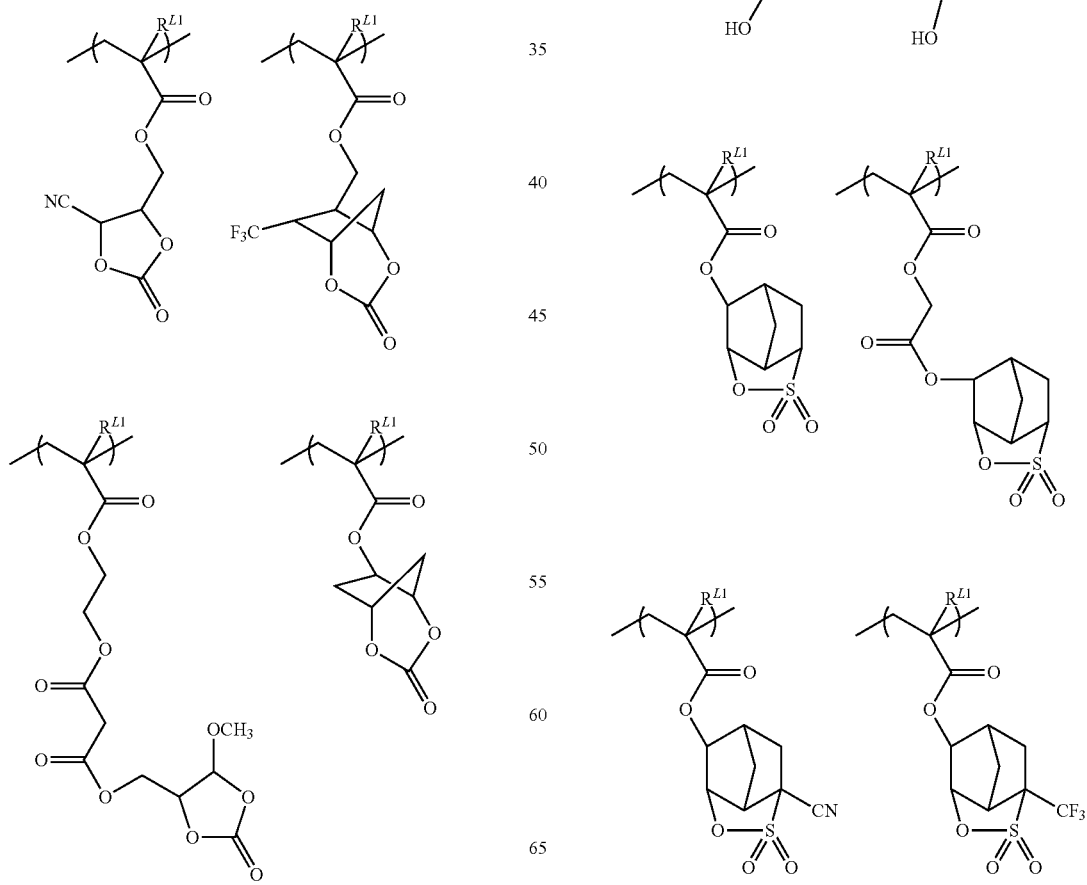

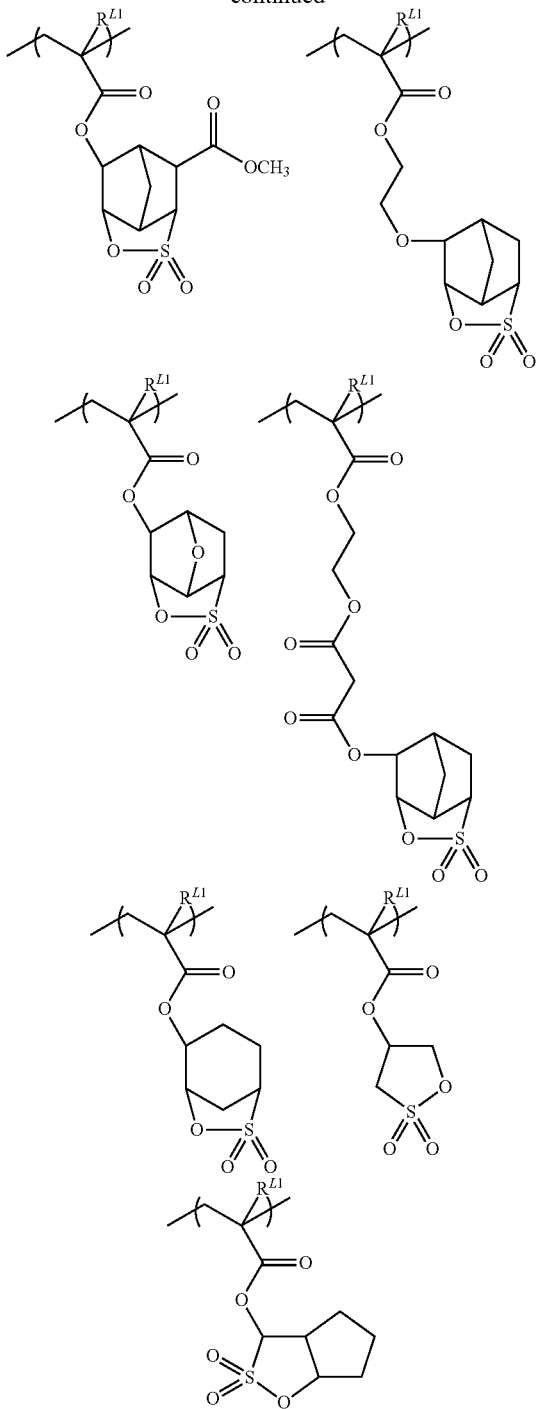

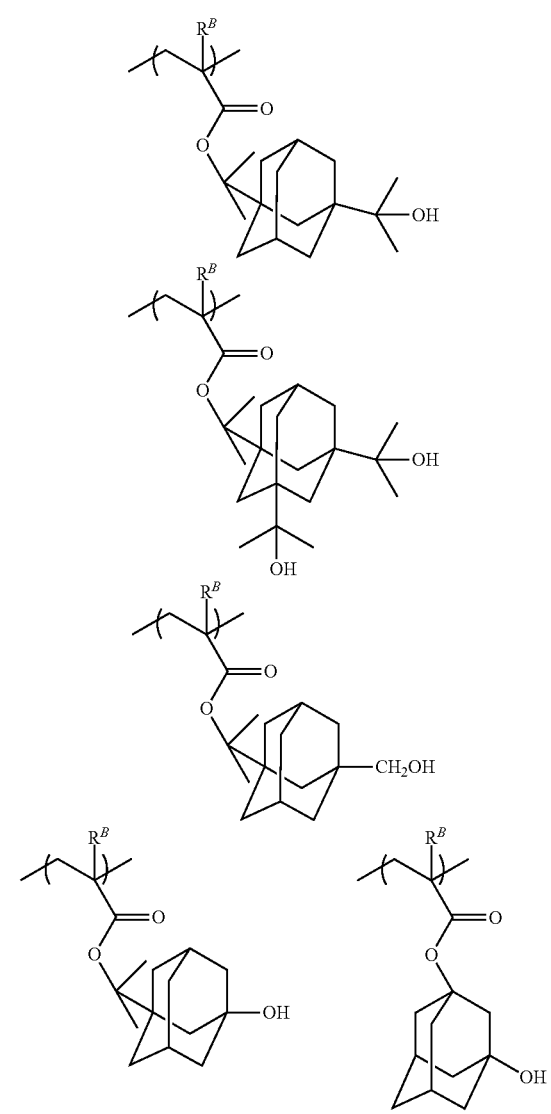

In the above formula, $R^{L1}$ represents a hydrogen atom, a fluorine atom, a methyl group or a trifluoromethyl group.

As the structural unit (II), of these: structural units that include a lactone structure and structural units that include a sultone structure are preferred; structural units that include a lactone structure are more preferred; structural units that include a norbornanelactone structure are still more preferred; and structural units derived from norbornanelactonyl (meth)acrylate are particularly preferred.

The proportion of the structural unit (II) contained with respect to the total structural units constituting the polymer (A) is preferably 0 mol % to 80 mol %, more preferably 20 mol % to 80 mol %, and still more preferably 30 mol % to 70 mol %. When the proportion of the structural unit (II) contained falls within the above range, more appropriate solubility of the polymer (A) in developer solutions may be attained. In addition, the adhesiveness of the resist pattern formed from the radiation-sensitive resin composition to a substrate may be further increased. When the proportion of the structural unit (II) contained is greater than the upper limit, pattern formability of the radiation-sensitive resin composition may be deteriorated.

Structural Unit (III)

The structural unit (III) is a structural unit having a polar group (except for those corresponding to the structural unit (II)). When the polymer (A) further has the structural unit (III), solubility in developer solutions may be adjusted.

Examples of the polar group include a hydroxy group, a carboxy group, a cyano group, a nitro group, a sulfonamide group, and the like. Of these, a hydroxy group and a carboxy group are preferred; and a hydroxy group is more preferred.

Examples of the structural unit (III) include structural units represented by the following formulae, and the like.

-continued

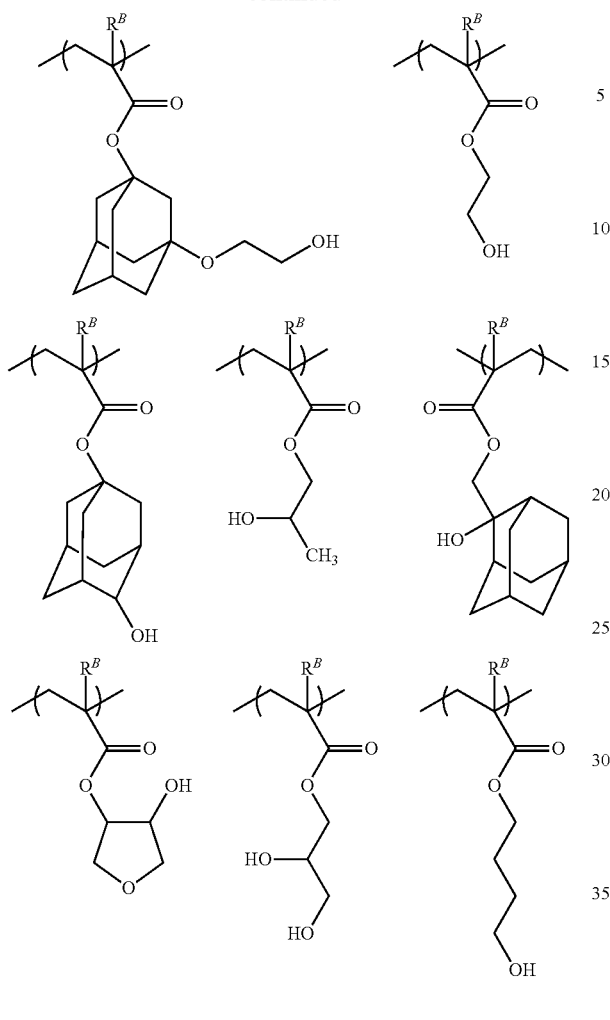

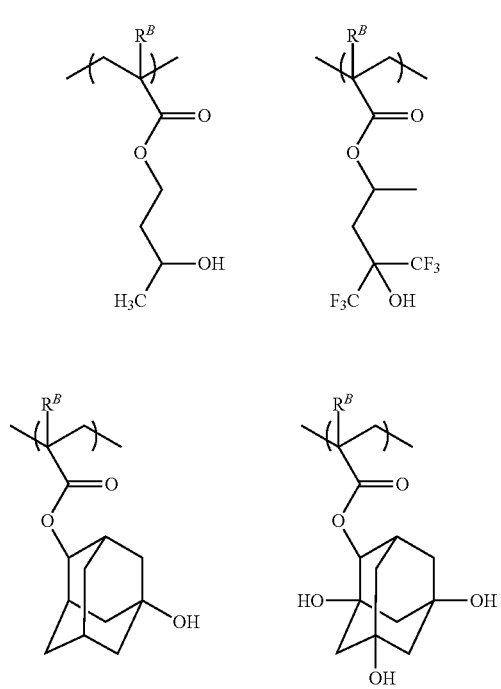

-continued

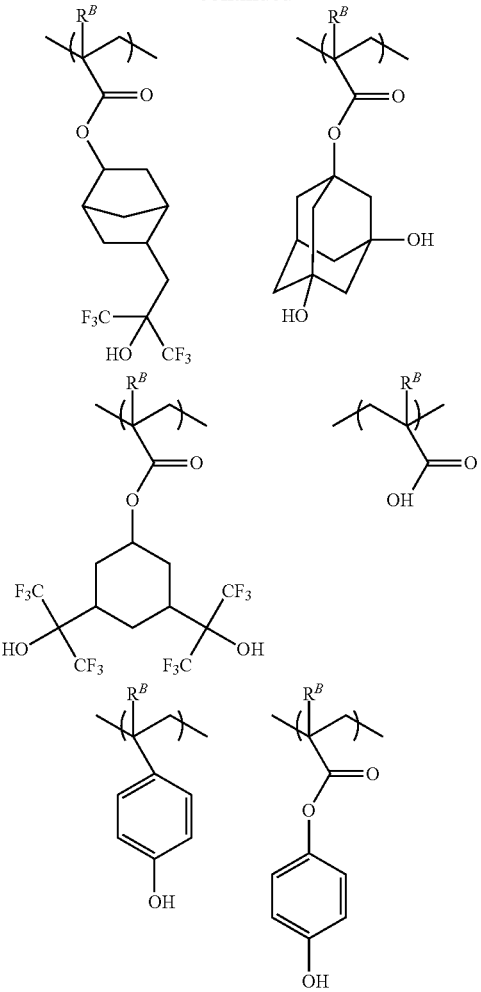

In the above formula, $R^B$ represents a hydrogen atom, a fluorine atom, a methyl group or a trifluoromethyl group.

The proportion of the structural unit (III) contained with respect to the total structural units constituting the polymer (A) is preferably 0 mol % to 80 mol %, more preferably 20 mol % to 75 mol %, and still more preferably 40 mol % to 70 mol %. When the proportion of the structural unit (III) contained falls within the above range, more appropriate solubility of the polymer (A) in developer solutions may be attained. When the proportion of the structural unit (III) contained is greater than the upper limit, pattern formability of the radiation-sensitive resin composition may be deteriorated.

Other Structural Unit

The polymer (A) may have other structural unit except for the structural units (I) to (III). The other structural unit is exemplified by structural units having a nondissociable alicyclic hydrocarbon group, and the like. The proportion of the other structural unit contained with respect to the total structural units constituting the polymer (A) is typically no greater than 30 mol %, and preferably no greater than 20 mol %. When the proportion of the other structural unit contained is greater than the upper limit, the pattern formability of the radiation-sensitive resin composition may be deteriorated.

The content of the polymer (A) with respect to the total solid content of the radiation-sensitive resin composition is preferably no less than 70% by mass, more preferably no less than 80% by mass, and still more preferably no less than 85% by mass.

Synthesis Method of Polymer (A)

The polymer (A) may be synthesized by, for example, polymerizing monomers that give each structural unit using a radical polymerization initiator in an appropriate solvent.

Examples of the radical polymerization initiator include: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide radical initiators such as benzoyl peroxide, t-butyl hydroperoxide and cumene hydroperoxide; and the like. Of these, AIBN and dimethyl 2,2'-azobisisobutyrate are preferred, and AIBN is more preferred. These radical initiators may be used either one type alone, or as a mixture of two or more types thereof.

Examples of the solvent which may be used in the polymerization include:

alkanes such as n-pentane, n-hexane, n-heptane, n-octane, n-nonane and n-decane;

cycloalkanes such as cyclohexane, cycloheptane, cyclooctane, decalin and norbornane;

aromatic hydrocarbons such as benzene, toluene, xylene, ethylbenzene and cumene;

halogenated hydrocarbons such as chlorobutanes, bromohexanes, dichloroethanes, hexamethylenedibromide and chlorobenzene;

saturated carboxylic acid esters such as ethyl acetate, n-butyl acetate, i-butyl acetate and methyl propionate;

ketones such as acetone, 2-butanone, 4-methyl-2-pentanone and 2-heptanone;

ethers such as tetrahydrofuran, diethoxyethanes and diethoxyethanes;

alcohols such as methanol, ethanol, 1-propanol, 2-propanol, 4-methyl-2-pentanol and propylene glycol monomethyl ether; and the like.

Of these, ketones and alcohols are preferred, and 2-butanone and propylene glycol monomethyl ether are more preferred. These solvents which may be used in the polymerization may be used either one type alone, or in combination of or two or more types thereof.

The reaction temperature in the polymerization is typically 40° C. to 150° C., and preferably 50° C. to 120° C. The time period of the reaction is typically 1 hour to 48 hours, and preferably 1 hour to 24 hours.

Although the polystyrene equivalent weight average molecular weight (Mw) of the polymer (A) as determined by gel permeation chromatography (GPC) is not particularly limited, the Mw is preferably no less than 1,000 and no greater than 50,000, more preferably no less than 2,000 and no greater than 30,000, still more preferably no less than 3,000 and no greater than 20,000, and particularly preferably no less than 5,000 and no greater than 15,000. When the Mw of the polymer (A) is less than the lower limit, the resultant resist film may have inferior heat resistance. When the Mw of the polymer (A) is greater than the upper limit, the resist film may have inferior developability.

The ratio (Mw/Mn) of the Mw to the polystyrene equivalent number average molecular weight (Mn) as determined by GPC of the polymer (A) is typically no less than 1 and no greater than 5, preferably no less than 1 and no greater than 3, and more preferably no less than 1 and no greater than 2.5.

The Mw and the Mn of the polymer herein are values determined with gel permeation chromatography (GPC) under the following conditions:

GPC columns: G2000HXL×2, G3000HXL×1 and G4000HXL×1 (manufactured by Tosoh Corporation)

column temperature: 40° C.

elution solvent: tetrahydrofuran (manufactured by Wako Pure Chemical Industries, Ltd.)

flow rate: 1.0 mL/min sample concentration: 1.0% by mass amount of injected sample: 100 µL detector: differential refractometer standard substance: mono-dispersed polystyrene.

The percentage content of the low-molecular weight matter (i.e., matter having a molecular weight of less than 1,000) in the polymer (A) is preferably no greater than 0.5% by mass, more preferably no greater than 0.2% by mass, and still more preferably no greater than 0.1% by mass. When the percentage content of the low-molecular weight matter in the polymer (A) falls within the above range, further favorable rectangularity of the cross-sectional shape, LWR performance, resolution and depth of focus of the radiation-sensitive resin composition can be attained.

The percentage content of the low-molecular weight matter in the polymer as referred to herein is a value determined by high performance liquid chromatography (HPLC) using an HPLC column (Intersil ODS-25 µm column (4.6 mm φ×250 mm), manufactured by GL Sciences, Inc.), under the following conditions.

elution solvent: acrylonitrile/0.1% by mass aqueous phosphoric acid solution flow rate: 1.0 mL/min sample concentration: 1.0% by mass amount of injected sample: 100 µL detector: differential refractometer (B) Acid Generator The acid generator (B) is a substance that generates an acid upon an exposure. This acid allows the acid-labile group in the polymer (A) to be dissociated, thereby giving a polar group such as a carboxy group. As a result, the solubility of the polymer (A) in a developer solution is altered. The acid generator (B) contained in the radiation-sensitive resin composition may be either in the form of a low-molecular compound as described later (hereinafter, may be also referred to as "acid generating agent (B)" ad libitum), or in the form of an acid generating group incorporated as a part of the polymer described later, or may be in both of these forms.

The acid generating agent (B) is exemplified by an onium salt compound, an N-sulfonyloxyimide compound, a halogen-containing compound, a diazo ketone compound, and the like.

The onium salt compound is exemplified by a sulfonium salt, a tetrahydrothiophenium salt, an iodonium salt, a phosphonium salt, a diazonium salt, a pyridinium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-bicyclo[2.2.1]hept-2-yl-1,1-difluoroethanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo

[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 6-(1-adamantanecarbonyloxy)-1,1,2,2-tetrafluorohexane-1-sulfonate, triphenylsulfonium 2-(adamantan-1-ylcarbonyloxy)-1,1,3,3,3-pentafluoropropane-1-sulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(4-n-butoxynaphthalen-1-yl)tetrahydrothiophenium camphorsulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyptetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyptetrahydrothiophenium camphorsulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, N-(2-(3-tetracyclo[4.4.0.1$^{2,5}$.1$^{7,10}$]dodecanyl)-1,1-difluoroethanesulfonyloxy)bicyclo[2.2.1]hept-5-ene-2,3-dicarboxyimide, N-(camphorsulfonyloxy)bicyclo[2.2.1]hept-5-ene-2,3-dicarboxyimide, and the like.

Among these, the acid generating agent (B) is preferably an onium salt compound, more preferably a sulfonium salt, and still more preferably triphenylsulfonium 2-(adamantan-1-ylcarbonyloxy)-1,1,3,3,3-pentafluoropropane-1-sulfonate.

When the acid generator (B) is an acid generating agent (B), in light of ensuring of the sensitivity and developability of the radiation-sensitive resin composition, the content of the acid generator (B) with respect to 100 parts by mass of the polymer (A) is preferably no less than 0.1 parts by mass and no greater than 30 parts by mass, more preferably no less than 0.5 parts by mass and no greater than 20 parts by mass, and still more preferably no less than 1 part by mass and no greater than 15 parts by mass. When the content of the acid generating agent (B) falls within the above range, the sensitivity and developability of the radiation-sensitive resin composition may be improved. One type, or two or more types of the acid generator (B) may be used.

(C) Acid Diffusion Control Agent

The acid diffusion control agent (C) is the acid diffusion control agent (I) according to the embodiment of the present invention. Due to containing the acid diffusion control agent (I) in addition to the polymer (A) and the acid generator (B), the radiation-sensitive resin composition is favorable in the LWR performance, the resolution, the rectangularity of the cross-sectional shape and the depth of focus. With regard to the acid diffusion control agent (C), explanation has been made in the above section of Acid Diffusion Control Agent (I). One type, or two or more types of the acid diffusion control agent (C) may be used.

The content of the acid diffusion control agent (C) with respect to the acid generating agent (B) is preferably 1 mol % to 100 mol %, more preferably 3 mol % to 70 mol %, and still more preferably 5 mol % to 50 mol %. When the content of the acid diffusion control agent (C) falls within the above range, the radiation-sensitive resin composition has more favorable LWR performance, resolution, rectangularity of the cross-sectional shape and depth of focus.

Moreover, the content of the acid diffusion control agent (C) with respect to 100 parts by mass of the polymer (A) is preferably no less than 0.1 parts by mass and no greater than 20 parts by mass, more preferably no less than 0.5 parts by mass and no greater than 15 parts by mass, and still more preferably no less than 1 part by mass and no greater than 10 parts by mass.

Optional Components (D) Other Acid Diffusion Controller

The radiation-sensitive resin composition may contain other acid diffusion controller (D) as needed. When the radiation-sensitive resin composition further contains the other acid diffusion controller (D) in addition to the acid diffusion control agent (C), more favorable LWR performance, resolution, rectangularity of the cross-sectional shape and depth of focus may be attained. Although the reason for being capable of further improving the aforementioned effects owing to containing the other acid diffusion controller (D) is not necessarily clear, it is assumed, for example, that a degree of diffusion of the compound as a whole constituting the acid diffusion control agent can be adjusted; and the like. The other acid diffusion controller (D) contained in the radiation-sensitive resin composition may be either in the form of an acid diffusion control agent that is a low-molecular compound as described later (hereinafter, may be also referred to as "(D) other acid diffusion control agent" ad libitum) or in the form of an acid diffusion control group incorporated as a part of the polymer described later, or may be in both of these forms.

The other acid diffusion control agent (D) is exemplified by a compound represented by the following formula (4) (hereinafter, may be also referred to as "nitrogen-containing compound (I)"), a compound having two nitrogen atoms within a single molecule (hereinafter, may be also referred to as "nitrogen-containing compound (II)", a compound having three nitrogen atoms within a single molecule (hereinafter, may be also referred to as "nitrogen-containing compound (III)"), an amide group-containing compound, a urea compound, a nitrogen-containing heterocyclic compound, and the like.

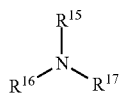
(4)

In the above formula (4), $R^{15}$, $R^{16}$ and $R^{17}$ each independently represent a hydrogen atom, a linear, branched or cyclic alkyl group, an aryl group or an aralkyl group that is each unsubstituted or substituted.

Examples of the nitrogen-containing compound (I) include: monoalkylamines such as n-hexylamine; dialkylamines such as di-n-butylamine; trialkylamines such as triethylamine; aromatic amines such as aniline; and the like.

Examples of the nitrogen-containing compound (II) include ethylenediamine, N,N,N',N'-tetramethylethylenediamine, and the like.

Examples of the nitrogen-containing compound (III) include: polyamine compounds such as polyethyleneimine and polyallylamine; polymers of dimethylaminoethylacrylamide, etc.; and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include pyridines such as pyridine and 2-methylpyridine, as well as pyrazine, pyrazole, and the like.

In addition, as the aforementioned nitrogen-containing organic compound, a compound having an acid-labile group may be also used. Examples of such a nitrogen-containing organic compound having an acid-labile group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl) diphenylamine, N-(t-butoxycarbonyl)-4-hydroxypiperidine, and the like.

Alternatively, as the other acid diffusion controller (D), a photodegradable base that generates a weak acid through photosensitization upon an exposure may be also used. The photodegradable base is exemplified by onium salt compounds and the like that lose acid diffusion controllability through degradation upon an exposure. Examples of the onium salt compound include sulfonium salt compounds represented by the following formula (5-1), iodonium salt compounds represented by the following formula (5-2), and the like.

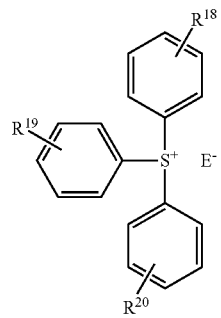
(5-1)

(5-2)

In the above formulae (5-1) and (5-2), $R^{18}$ to $R^{22}$ each independently represent a hydrogen atom, an alkyl group, an alkoxy group, a hydroxy group or halogen atom; $E^-$ and $Q^-$ each independently represent $OH^-$, $R^\alpha$—$COO^-$, $R^\alpha$—$SO_3^-$ or an anion represented by the following formula (6-3), wherein $R^\alpha$ represents an alkyl group, an aryl group or an aralkyl group.

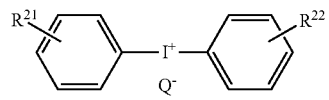
(5-3)

In the above formula (5-3), $R^{23}$ represents a linear or branched alkyl group having 1 to 12 carbon atoms, or a linear or branched alkoxyl group having 1 to 12 carbon atoms, wherein a part or all of hydrogen atoms of these are optionally substituted with a fluorine atom; and u is an integer of 0 to 2.

When the other acid diffusion controller (D) is the other acid diffusion control agent (D), the content of the other acid diffusion controller (D) with respect to the acid generating agent (B) is preferably 0 mol % to 300 mol %, more preferably 5 mol % to 250 mol %, and still more preferably 10 mol % to 200 mol %. When the content of the other acid diffusion control agent (D) falls within the above range, more favorable sensitivity, LWR performance, resolution, rectangularity of the cross-sectional shape and depth of focus of the radiation-sensitive resin composition may be attained. When the content of the other acid diffusion control agent (D) is greater than the upper limit, the sensitivity of the radiation-sensitive resin composition may be impaired.

Also, the content of the other acid diffusion control agent (D) with respect to 100 parts by mass of the polymer (A) is preferably 0 to 10 parts by mass, more preferably 0.1 parts by mass to 8 parts by mass, and still more preferably 0.3 parts by mass to 5 parts by mass.

(E) Fluorine Atom-Containing Polymer

The radiation-sensitive resin composition may contain the fluorine atom-containing polymer (E) (except for those corresponding to the polymer (A)). When the radiation-sensitive resin composition contains the fluorine atom-containing polymer (E), upon forming a resist film, due to a repellent characteristic of the fluorine atom-containing polymer (E) in the resist film, the distribution thereof tends to be uneven distributed in the vicinity of the surface of the resist film, and thus elution of the acid generating agent, the acid diffusion control agent and/or the like into a liquid immersion medium during liquid immersion lithography can be inhibited. In addition, owing to a water repellent characteristic feature of the fluorine atom-containing polymer (E), an advancing contact angle of a liquid immersion medium on a resist coating film can be adjusted to fall within a desired range, thereby enabling occurrence of bubble defects to be inhibited. Moreover, a receding contact angle of a liquid immersion medium on the resist film is increased, and therefore, a high-speed scanning exposure is enabled without the remanence of water droplets. When the radiation-sensitive resin composition thus contains the fluorine atom-containing polymer (E), a resist coating film suited for a liquid immersion lithography process may be formed.

Although the fluorine atom-containing polymer (E) is not particularly limited as long as it is a polymer having a fluorine atom, the fluorine atom-containing polymer (E) preferably has a percentage content of fluorine atoms (% by mass) greater than that of the polymer (A) in the radiation-sensitive resin composition. When the percentage content of fluorine atoms of the fluorine atom-containing polymer (E) is greater than that of the polymer (A), the degree of the uneven distribution described above is further increased, whereby characteristics of the resist film such as water repellency and elution inhibitory ability can be improved.

The percentage content of fluorine atoms in the fluorine atom-containing polymer (E) is preferably no less than 1% by mass, more preferably 2% by mass to 60% by mass, still more preferably 4% by mass to 40% by mass, and particularly preferably 7% by mass to 30% by mass. When the percentage content of fluorine atoms of the fluorine atom-containing polymer (E) is less than the lower limit, the hydrophobicity of the surface of the resist film may be decreased. It is to be noted that the percentage content of fluorine atoms (% by mass) in the polymer may be determined by a measurement on a $^{13}$C-NMR spectrum to decide a polymer structure, followed by calculation based on the structure.

The fluorine atom-containing polymer (E) preferably has at least one selected from the group consisting of the following structural unit (Ea) and structural unit (Eb). The fluorine atom-containing polymer (E) may have each one type, or two or more types of the structural unit (Ea) and the structural unit (Eb).

Structural Unit (Ea)

The structural unit (Ea) is represented by the following formula (6a). When the fluorine atom-containing polymer (E) has the structural unit (Ea), the percentage content of fluorine atoms can be adjusted.

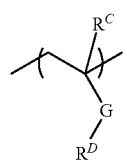

(6a)

In the above formula (6a), $R^C$ represents a hydrogen atom, a methyl group or a trifluoromethyl group; G represents a single bond, an oxygen atom, a sulfur atom, —CO—O—, —SO$_2$—O—NH—, —CO—NH— or —O—CO—NH—;

$R^D$ represents a monovalent chain hydrocarbon group having 1 to 6 carbon atoms and having at least one fluorine atom, or a monovalent aliphatic cyclic hydrocarbon group having 4 to 20 carbon atoms and having at least one fluorine atom.

Examples of the chain hydrocarbon group having 1 to 6 carbon atoms and having at least one fluorine atom which may be represented by $R^D$ include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro-n-propyl group, a perfluoro-1-propyl group, a perfluoro-n-butyl group, a perfluoro-1-butyl group, a perfluoro-t-butyl group, a 2,2,3,3,4,4,5,5-octafluoropentyl group, a perfluorohexyl group, and the like. Of these, a trifluoromethyl group, a 2,2,2-trifluoroethyl group and a 1,1,1,3,3,3-hexafluoropropyl group are preferred, and a 2,2,2-trifluoroethyl group is more preferred.

Examples of the aliphatic cyclic hydrocarbon group having 4 to 20 carbon atoms and having at least one fluorine atom which may be represented by $R^D$ include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

Examples of the monomer that gives a structural unit (Ea) include a trifluoromethyl (meth)acrylic acid ester, 2,2,2-trifluoroethyl (meth)acrylic acid ester, perfluoroethyl (meth)acrylic acid ester, perfluoro-n-propyl (meth)acrylic acid ester, perfluoro-1-propyl (meth)acrylic acid ester, perfluoro-n-butyl (meth)acrylic acid ester, perfluoro-1-butyl (meth)acrylic acid ester, perfluoro-t-butyl (meth)acrylic acid ester, 2-(1,1,1,3,3,3-hexafluoropropyl)(meth)acrylic acid ester, 1-(2,2,3,3,4,4,5,5-octafluoropentyl)(meth)acrylic acid ester, perfluorocyclohexylmethyl (meth)acrylic acid ester, 1-(2,2,3,3,3-pentafluoropropyl)(meth)acrylic acid ester, monofluorocyclopentyl (meth)acrylic acid ester, difluorocyclopentyl (meth)acrylic acid ester, perfluorocyclopentyl (meth)acrylic acid ester, monofluorocyclohexyl (meth)acrylic acid ester, difluorocyclopentyl (meth)acrylic acid ester, perfluorocyclohexylmethyl (meth)acrylic acid ester, fluoronorbornyl (meth)acrylic acid ester, fluoroadamantyl (meth)acrylic acid ester, fluorobornyl (meth)acrylic acid ester, fluoroisobornyl (meth)acrylic acid ester, fluorotricyclodecyl (meth)acrylic acid ester, fluorotetracyclodecyl (meth)acrylic acid ester, and the like.

Of these, trifluoromethyl (meth)acrylic acid ester, 2,2,2-trifluoroethyl (meth)acrylic acid ester and 2-(1,1,1,3,3,3-hexafluoropropyl)(meth)acrylic acid ester are preferred, and 2,2,2-trifluoroethyl (meth)acrylic acid ester is more preferred.

The proportion of the structural unit (Ea) contained with respect to the total structural units constituting the fluorine atom-containing polymer (E) is preferably 5 mol % to 80 mol %, more preferably 10 mol % to 60 mol %, and still more preferably 15 mol % to 40 mol %. The proportion of the structural unit (Ea) contained falling within the above range leads to a greater dynamic contact angle on the surface of a resist coating film exhibited when subjected to exposure through liquid immersion lithography.

Structural Unit (Eb)

The structural unit (Eb) is represented by the following formula (6b). The fluorine atom-containing polymer (E) has enhanced hydrophobicity when the structural unit (Eb) is included; therefore, a more favorable dynamic contact angle on the surface of a resist film formed from the radiation-sensitive resin composition may be attained.

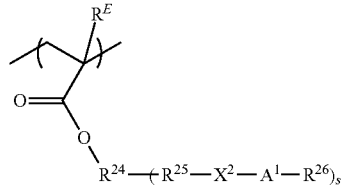

(6b)

In the above formula (6b), $R^E$ represents a hydrogen atom, a methyl group or a trifluoromethyl group; $R^{24}$ represents a hydrocarbon group having a valency of (s+1) and having 1 to 20 carbon atoms, and a structure in which $R^{24}$ has an oxygen atom, a sulfur atom, —NR'— (wherein R' represents a hydrogen atom or a monovalent organic group), a carbonyl group, —CO—O— or —CO—NH— which is bound to an end of $R^{25}$ side; $R^{25}$ represents a single bond, a divalent chain hydrocarbon group having 1 to 10 carbon atoms or a divalent aliphatic cyclic hydrocarbon group having 4 to 20 carbon atoms; $X^2$ represents a divalent chain hydrocarbon group having 1 to 20 carbon atoms and having at least one fluorine atom; $A^1$ represents an oxygen atom, —NR"—, —CO—O—* or —SO$_2$—O—*; R" represents a hydrogen atom or a monovalent organic group (wherein "*" denotes a binding site to $R^{26}$); $R^{26}$ represents a hydrogen atom or a monovalent organic group; s is an integer of 1 to 3, wherein in a case where s is 2 or 3, a plurality of $R^{25}$s, $X^2$s, $A^1$s and $R^{26}$s are each identical or different with each other.

$R^{26}$ preferably represents a hydrogen atom since the solubility of the fluorine atom-containing polymer (E) in an alkaline developer solution can be enhanced.

The monovalent organic group which may be represented by $R^{26}$ is exemplified by hydrocarbon groups having 1 to 30 carbon atoms which may have an acid-labile group, an alkali-labile group or a substituent, and the like.

The structural unit (Eb) is exemplified by structural units represented by the following formulae (6b-1) to (6b-3), and the like.

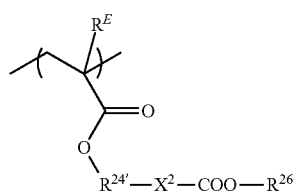

(6b-1)

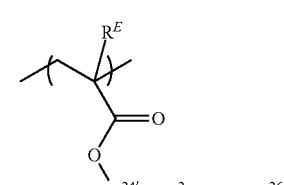

(6b-2)

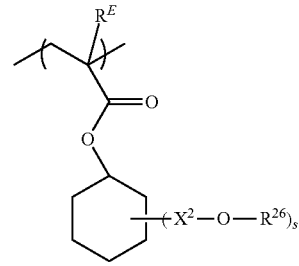

(6b-3)

In the above formulae (6b-1) to (6b-3), $R^{24'}$ represents a divalent linear, branched or cyclic saturated or unsaturated hydrocarbon group having 1 to 20 carbon atoms; $R^E$, $X^2$, $R^{26}$ and s are as defined in the above formula (6b). wherein in a case where s is 2 or 3, a plurality of $X^2$s and $R^{26}$s are each identical or different with each other.

The proportion of the structural unit (Eb) contained with respect to the total structural units constituting the fluorine atom-containing polymer (E) is preferably 0 mol % to 90 mol %, more preferably 0 mol % to 80 mol %, and still more preferably 10 mol % to 70 mol %. When the proportion of the structural unit (Eb) contained falls within the above range, the surface of a resist film formed from the radiation-sensitive resin composition can achieve a more favorable extent of a decrease of a dynamic contact angle in a development with an alkali.

Structural Unit (Ec)

The fluorine atom-containing polymer (E) may have a structural unit that includes an acid-labile group, except for those corresponding to the structural unit (Eb), (hereinafter, may be also referred to as "structural unit (Ec)"), in addition to the structural units (Ea) and (Eb) described above. When the fluorine atom-containing polymer (E) has the structural unit (Ec), remaining of undissolved fluorine atom-containing polymer (E) in the resist film into the developer solution can be inhibited, and consequently, occurrence of development defects in the resultant resist pattern can be prevented. The structural unit (Ec) is exemplified by those exemplified as the structural unit (I) in the polymer (A) described above, and the like.

The proportion of the structural unit (Ec) contained with respect to the total structural units constituting the fluorine atom-containing polymer (E) is preferably 10 mol % to 90 mol %, more preferably 20 mol % to 85 mol %, and still more preferably 25 mol % to 80 mol %. When the proportion of the structural unit (Ec) contained is less than the lower limit, occurrence of the development defects in the resist pattern may not be satisfactorily inhibited. When the proportion of the structural unit (Ec) contained is greater than the upper limit, hydrophobicity of the surface of the resultant resist film may be decreased.

Other Structural Unit

Also, the fluorine atom-containing polymer (E) may have other structural unit such as e.g., a structural unit that includes an alkali-soluble group, a structural unit that includes at least one structure selected from the group consisting of a lactone structure, a cyclic carbonate structure and a sultone structure, and a structural unit that includes an acid-nonlabile alicyclic group, in addition to the structural unit(s) described above. Examples of the alkali-soluble group include a carboxy group, a sulfonamide group, a sulfo group, and the like. The structural unit that includes at least one structure selected from the group consisting of a lactone structure, a cyclic carbonate structure and a sultone structure is exemplified by the structural unit (II) in the polymer (A) described above, and the like.

The proportion of the other structural unit contained with respect to the total structural units constituting the fluorine atom-containing polymer (E) is typically no greater than 30 mol %, and preferably no greater than 20 mol %. When the proportion of the other structural unit contained is greater than the upper limit, the pattern formability of the radiation-sensitive resin composition may be deteriorated.

The content of the fluorine atom-containing polymer (E) in the radiation-sensitive resin composition with respect to 100 parts by mass of the polymer (A) is preferably 0 to 20 parts by mass, more preferably 0.5 parts by mass to 15 parts by mass, and still more preferably 1 part by mass to 10 parts by mass. When the content of the fluorine atom-containing polymer (E) is greater than the upper limit, the pattern formability of the radiation-sensitive resin composition may be deteriorated.

(F) Solvent

The radiation-sensitive resin composition usually contains the solvent (F). The solvent (F) is not particularly limited as long as it is a solvent capable of dissolving or dispersing at least the polymer (A), the acid generator (B) and the acid diffusion control agent (C), as well as the other acid diffusion controller (D) which is contained as desired, and the like.

The solvent (F) is exemplified by an alcohol solvent, an ether solvent, a ketone solvent, an amide solvent, an ester solvent, a hydrocarbon solvent, and the like.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol and benzyl alcohol and, diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ether solvent include:

dialkyl ether solvents such as diethyl ether, dipropyl ether and dibutyl ether;

cyclic ether solvents such as tetrahydrofuran and tetrahydropyran;

aromatic ring-containing ether solvents such as diphenyl ether and anisole (methyl phenyl ether); and the like.

Examples of the ketone solvent include:

chain ketone solvents such as acetone, methyl ethyl ketone, methyl-n-propyl ketone, methyl-n-butyl ketone, diethyl ketone, methyl-iso-butyl ketone, 2-heptanone (methyl-n-pentyl ketone), ethyl-n-butyl ketone, methyl-n-hexyl ketone, di-iso-butyl ketone and trimethylnonanone:

cyclic ketone solvents such as cyclopentanone, cyclohexanone, cycloheptanone, cyclooctanone and methylcyclohexanone:

2,4-pentanedione, acetonyl acetone, acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

acetic acid ester solvents such as methyl acetate, ethyl acetate, n-propyl acetate, iso-propyl acetate, n-butyl acetate, iso-butyl acetate, sec-butyl acetate, n-pentyl acetate, i-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

carbonate solvents such as diethyl carbonate;

glycol diacetate, methoxytriglycol acetate, ethyl propionate, n-butyl propionate, iso-amyl propionate, diethyl oxalate, di-n-butyl oxalate, methyl acetoacetate, ethyl acetoacetate, methyl lactate, ethyl lactate, n-butyl lactate, n-amyl lactate, diethyl malonate, dimethyl phthalate and diethyl phthalate, and the like.

Examples of the hydrocarbon solvent include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Of these, ester solvents and ketone solvents are preferred; polyhydric alcohol partial ether acetate solvents and cyclic ketone solvents are more preferred; and propylene glycol monomethyl ether acetate and cyclohexanone are even more preferred. The radiation-sensitive resin composition may contain one type, or two or more types of the solvent (F).

Other Optional Components

The radiation-sensitive resin composition may contain other optional component(s) in addition to the components (A) to (F) described above. The other optional component is exemplified by an uneven distribution accelerator, a surfactant, an alicyclic skeleton-containing compound, a sensitizing agent; and the like. Each one type, or two or more types in combination of these other optional components may be used.

Uneven Distribution Accelerator

The uneven distribution accelerator has an effect of more efficiently segregating the fluorine atom-containing polymer (E) on the surface of a resist film. When the radiation-sensitive resin composition contains the uneven distribution accelerator, the amount of the fluorine atom-containing polymer (E) added can be decreased than before. Therefore, elution of the component from the resist film into the liquid immersion medium is further inhibited, and quicker exposure through liquid immersion lithography is enabled by high-speed scanning, without impairing characteristics such as the rectangularity of the cross-sectional shape, the LWR performance and the resolution and the depth of focus. As a result, the hydrophobicity of the surface of a resist film that prevents defects derived from liquid immersion such as watermark defects can be improved. As such an uneven distribution accelerator, a low-molecular compound having a relative permittivity of no less than 30 and no greater than 200, and having a boiling point at 1 atmospheric pressure of no less than 100° C. may be used. Specifically, such a compound is exemplified by a lactone compound, a carbonate compound, a nitrile compound, a polyhydric alcohols, and the like.

Examples of the lactone compound include γ-butyrolactone, valerolactone, mevalonic lactone, norbornanelactone, and the like.

Examples of the carbonate compound include propylene carbonate, ethylene carbonate, butylene carbonate, vinylene carbonate, and the like.

Examples of the nitrile compound include succinonitrile, and the like.

Examples of the polyhydric alcohol include glycerin, and the like.

As the uneven distribution accelerator, of these, lactone compounds are preferred, and γ-butyrolactone is more preferred.

The content of the uneven distribution accelerator in the radiation-sensitive resin composition with respect to 100 parts by mass of the total amount of the polymers is preferably 10 parts by mass to 500 parts by mass, more preferably 15 parts by mass to 300 parts by mass, and still more preferably 20 parts by mass to 100 parts by mass.

Surfactant

The surfactant exerts the effect of improving a coating property, striation, developability and the like. Examples of the surfactant include: nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; commercially available products such as KP341 (manufactured by Shin-Etsu Chemical Co., Ltd.); Polyflow No. 75 and No. 95 (each manufactured by Kyoeisha Chemical Co., Ltd.); EFTOP EF301, EF303 and EF352 (each manufactured by Tochem Products Co. Ltd.); Megaface F171 and F173 (each manufactured by Dainippon Ink and Chemicals, Incorporated); Fluorad FC430 and FC431 (each manufactured by Sumitomo 3M Limited); ASAHI GUARD AG710, Surflon S-382, SC-101, SC-102, SC-103, SC-104, SC-105 and SC-106 (each manufactured by Asahi Glass Co., Ltd.); and the like. The content of the surfactant in the radiation-sensitive resin composition with respect to 100 parts by mass of the polymer (A) is typically no greater than 2 parts by mass.

Alicyclic Skeleton-Containing Compound

The alicyclic skeleton-containing compound exhibits an effect of improving the dry etching resistance, pattern configuration, adhesiveness to a substrate, and the like.

Examples of the alicyclic skeleton-containing compound include:

adamantane derivatives such as 1-adamantanecarboxylic acid, 2-adamantanone and t-butyl 1-adamantanecarboxylate;

deoxycholic acid esters such as t-butyl deoxycholate, t-butoxycarbonylmethyl deoxycholate and 2-ethoxyethyl deoxycholate;

lithocholic acid esters such as t-butyl lithocholate, t-butoxycarbonylmethyl lithocholate and 2-ethoxyethyl lithocholate;

3-[2-hydroxy-2,2-bis(trifluoromethyl)ethyl]tetracyclo[4.4.0.1$^{2,5}$.1$^{7,10}$]dodecane, 2-hydroxy-9-methoxycarbonyl-5-oxo-4-oxa-tricyclo[4.2.1.0$^{3,7}$]nonane; and the like. The content of the alicyclic skeleton-containing compound in the radiation-sensitive resin composition with respect to 100 parts by mass of the polymer (A) is typically no greater than 5 parts by mass.

Sensitizing Agent

The sensitizing agent has an action of increasing the amount of production of the acid from the acid generating agent (B), etc., and thus has an effect of improving "apparent sensitivity" of the radiation-sensitive resin composition.

Examples of the sensitizing agent include carbazoles, acetophenones, benzophenones, naphthalenes, phenols, biacetyl, eosin, rose bengal, pyrenes, anthracenes, phenothiazines, and the like. These sensitizing agents may be used either alone, or two or more types thereof may be used in combination. The content of the sensitizing agent in the radiation-sensitive resin composition with respect to 100 parts by mass of the polymer (A) is typically no greater than 2 parts by mass.

Preparation Method of Radiation-Sensitive Resin Composition

The radiation-sensitive resin composition may be prepared by, for example, mixing the polymer (A), the acid generator (B) and the acid diffusion control agent (C), and further optional component(s) and the solvent (F) which may be Included as needed at a certain ratio. The radiation-sensitive resin composition is preferably filtered after the mixing through, for example, a filter or the like having a pore size of about 0.2 μm. The solid content concentration of the radiation-sensitive resin composition is typically 0.1% by mass to 50% by mass, preferably 0.5% by mass to 30% by mass, and more preferably 1% by mass to 20% by mass.

Resist Pattern-Forming Method

The resist pattern-forming method according to another embodiment of the present invention includes:

providing a resist film using the radiation-sensitive resin composition step (hereinafter, may be also referred to as "resist film-providing step");

exposing the resist film (hereinafter, may be also referred to as "exposure step"); and developing the resist film exposed (hereinafter, may be also referred to as "development step").

According to the resist pattern-forming method, since the radiation-sensitive resin composition described above is used, while exhibiting a great depth of focus, resist pattern can be formed having a small LWR, a superior rectangularity of the cross-sectional shape and a high resolution. Each step will be explained below.

Resist Film-Providing Step

In this step, a resist film is provided using the radiation-sensitive resin composition. The substrate on which the resist film is provided may be exemplified by a silicon wafer, a wafer coated with silicon dioxide, an antireflective film, and the like. The coating process of the radiation-sensitive resin composition is exemplified by the process of spin-coating, cast coating, roll coating, and the like. It is preferred that the solvent in the coating film is eliminated through evaporation by subjecting the coating film provided by the coating to prebaking (PB). The temperature of PB is typically 60° C. to 140° C., and preferably 80° C. to 120° C. The time period of PB is typically 5 sec to 600 sec, and preferably 10 sec to 300 sec.

Exposure Step

In this step, the resist film provided in the resist film forming step is exposed. This exposure is carried out by irradiation with an exposure light through a photomask, etc., (as the case may be, through a liquid immersion medium such as water). Examples of the exposure light include electromagnetic waves such as visible light rays, ultraviolet rays, far ultraviolet rays, extreme ultraviolet rays, X-rays and γ-rays; charged particle rays such as electron beams and α-rays, and the like, which may be selected in accordance with a line width of the intended pattern. Of these, far ultraviolet rays, extreme ultraviolet rays and electron beams are preferred; an ArF excimer laser beam (wavelength: 193 nm), a KrF excimer laser beam (wavelength: 248 nm), EUV (13.5 nm) and an electron beam are more preferred; and an ArF excimer laser beam and an electron beam are still more preferred.

After the exposure, it is preferred that post exposure baking (PEB) is carried out to facilitate dissociation of the acid-labile group of the polymer (A) at an exposed region of the resist film by way of the acid generated from the acid generator (B) by an exposure. This PEB enables the difference of solubilities in a developer solution to be certainly generated between the region exposed (light-exposed site) and the region not exposed (light-unexposed site). The temperature of PEB is typically 50° C. to 180° C., and preferably 80° C. to 130° C. The time period of PEB is typically 5 sec to 600 sec, and preferably 10 sec to 300 sec.

When the exposure through liquid immersion lithography is to be carried out, in order to prevent direct contact of the resist film with the liquid immersion medium before the exposure step, a protective film for liquid immersion which is insoluble in the liquid immersion medium may be provided on the resist film. As the protective film for liquid immersion, either a solvent-peelable protective film that is peeled by a solvent prior to the development step (for example, see Japanese Unexamined Patent Application, Publication No. 2006-227632), or a developer solution-peelable protective film that is peeled concomitant with the development in the development step (for example, see WO 2005-069076 and WO 2006-035790) may be used. However, in light of the throughput, a developer solution-peelable protective film for liquid immersion is preferably used.

Development Step

In the development step, the resist film exposed in the exposure step is developed. Thus, a predetermined resist pattern is formed. The development process may be executed either by a development with an alkali or a development with an organic solvent. In general, a positive type resist pattern is formed by the development with an alkali, whereas a negative type resist pattern is formed by the development with an organic solvent. After the development, washing with a rinse agent such as water or alcohol followed by drying is generally carried out.

In the case of the development with an alkali, examples of the developer solution include aqueous alkaline solutions prepared by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene or 1,5-diazabicyclo-[4.3.0]-5-nonene, and the like. Of these, aqueous TMAH solutions are preferred, and a 2.38% by mass aqueous TMAH solution is more preferred.

Furthermore, in the case of the development with an organic solvent, examples of the developer solution include organic solvents such as a hydrocarbon solvent, an ether solvent, an ester solvent, a ketone solvent and an alcohol solvent, and solvents containing the organic solvent. The organic solvent is exemplified by one, or two or more types of the solvents illustrated as the solvent (F) for the radiation-sensitive resin composition described above, and the like. Of these, an ester solvent and a ketone solvent are preferred. The ester solvent is preferably an ester acetate solvent, and more preferably n-butyl acetate. The ketone solvent is preferably a chain ketone, and more preferably 2-heptanone.

Compound

The compound according to still other embodiment of the present invention is the compound (1) and the compound (2). Due to having the properties described above, the compound can be suitably used as an acid diffusion control agent, and the radiation-sensitive resin composition containing the compound is favorable in the LWR performance, the resolution, the rectangularity of the cross-sectional shape and the depth of focus. The compound is described in the section "Acid Diffusion Control Agent" (I) presented above.

Production Method of Compound

The production method of the compound according to yet other embodiment of the present invention involves:

a production method of the compound (1), the method including reacting a compound represented by the above formula (i-a) and an amine compound represented by the above formula (i-b); and a production method of the compound (2), the method including reacting a compound represented by the above formula (ii-a) and an amine compound represented by the above formula (ii-b).

According to the production method of the compound, the compound (I) can be conveniently produced. With respect to the production method of the compound, explanation has been made in the section "Acid Diffusion Control Agent" (I) presented above.

EXAMPLES

Hereinafter, the present invention is explained in detail by way of Examples, but, the present invention is not in any way limited by Examples. Measuring methods for various types of physical properties are shown below.

Weight Average Molecular Weight (Mw), Number Average Molecular Weight (Mn) and Dispersity Index (Mw/Mn)

The Mw and Mn of the polymer were determined with gel permeation chromatography (GPC) using GPC columns (G2000HXL×2, G3000HXL×1 and G4000HXL×1; manufactured by Tosoh Corporation) under the following conditions. In addition, the dispersity index (Mw/Mn) was calculated from the measurement results of the Mw and the Mn.

elution solvent: tetrahydrofuran
flow rate: 1.0 mL/min
sample concentration: 1.0% by mass amount of injected sample: 100 μL
column temperature: 40° C.
detector: differential refractometer
standard substance: mono-dispersed polystyrene Percentage Content of Low-Molecular Weight Matter The percentage content of (% by mass) of the low-molecular weight matter (i.e., the matter having a molecular weight of less than 1,000) in the polymer (A) was determined with high performance liquid chromatography (HPLC) using an HPLC column (Intersil ODS-25 μm column (4.6 mm φ×250 mm); manufactured by GL Sciences, Inc.) under the following conditions:
elution solvent: acetonitrile/0.1% by mass aqueous phosphoric acid solution
flow rate: 1.0 mL/min
sample concentration: 1.0% by mass
amount of injected sample: 100 μL
detector: differential refractometer.

$^{13}$C-NMR Analysis

The $^{13}$C-NMR analytic measurement for determining the proportion of each constitutional unit contained in the polymer was carried out using a nuclear magnetic resonance apparatus (manufactured by JNM-ECX400, JEOL, Ltd.).

Synthesis of Compound (I)

The compound (I) was synthesized in accordance with the following reaction scheme.

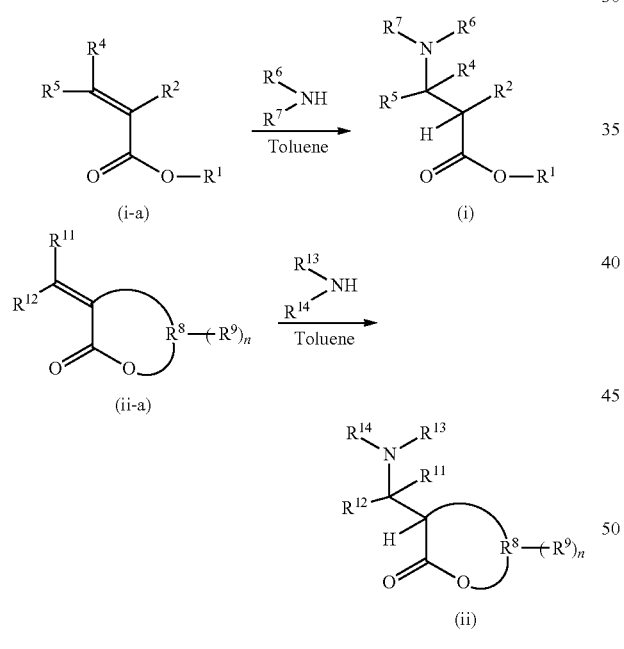

In the above scheme, $R^1$ represents a cyclohexyl group, a 1-adamantyl group, a 8-tricyclodecyl group, a 3-hydroxy-1-adamantyl group, a norbornanelacton-yl group, a norbornanesulton-yl group, a norbornanelacton-yloxycarbonylmethyl group, a 2-i-propyl-2-adamantyl group, a 2-methyl-2-adamantyl group, a 1-i-propyl-1-cyclopentyl group, a 1,3-dioxa-2,2-dimethylcyclopentan-5-ylmethyl group, a 7-(1,3-dioxa-2,2-dimethylcyclopentan-4-yl)-3,3-dimethyl-2,4,8-trioxabicyclo[3,3,0]octan-6-yl group or a 7-(1,3-dioxa-spiro[adamantane-2,2']cyclopentan-4-yl)-spiro[adamantane-3,3']-2,4,8-trioxabicyclo[3,3,0]octan-6-yl group;

$R^2$ represents a methyl group;

$R^4$ and $R^5$ represent a hydrogen atom;

$R^6$ and $R^7$ represent an ethyl group, or $R^6$ and $R^7$ taken together represent a piperidine structure, a morpholine structure or a decahydroquinoline structure through binding with each other together with the nitrogen atom to which $R^6$ and $R^7$ bond;

$R^8$ is a group that taken together represents a butyrolactone-triyl group or a butyrolactone-tetrayl group together with the ester group and the α-carbon atom thereof;

$R^9$ represents a cyclohexan-1,1-diyl group, a 2-methyl-1-oxacyclopentan-3,3-diyl group or an adamantan-2,2-diyl group;

$R^{11}$ and $R^{12}$ represent a hydrogen atom or a methyl group; and $R^{13}$ and $R^{14}$ taken together represent a piperidine structure through binding with each other together with the nitrogen atom to which $R^{13}$ and $R^{14}$ bond.

Example 1

After 16.8 g (100 mmol) of cyclohexyl methacrylate, 25.6 g (300 mmol) of piperidine and 20 g of toluene were charged into a 100 mL eggplant-shaped flask, and the mixture was heated at 65° C. for 36 hour with stirring to allow the reaction to proceed. After completion of the reaction, water was added to the reaction liquid, and the organic layer was washed with water seven times by liquid separating operation. Next, the organic layer was dried over anhydrous sodium sulfate, and the solvent was distilled off to give a light yellow oily matter. The oily matter was purified on column chromatography to obtain 18.4 g (yield: 72.8%) of a compound represented by the following formula (i-1) as colorless oily matter.

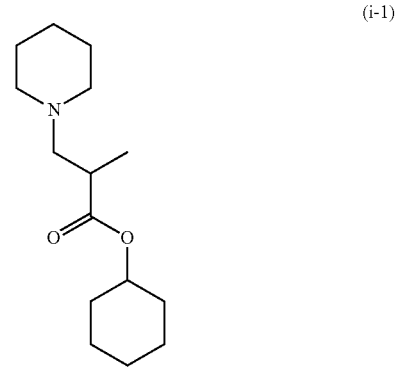 [SMILES: CC(CN1CCCCC1)C(=O)OC1CCCCC1]

Examples 2 to 21

Compounds represented by the following formulae (i-2) to (i-17), and compounds represented by the following formulae (ii-1) to (ii-4) were synthesized, respectively in a similar manner to Example 1 except that each (meth)acrylic acid ester or α-methylene butyrolactone was used in place of cyclohexyl methacrylate, and each amine compound was used in place of piperidine in Example 1.

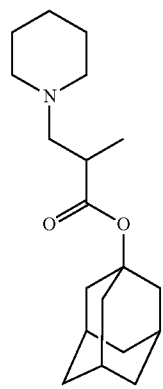 (i-2)
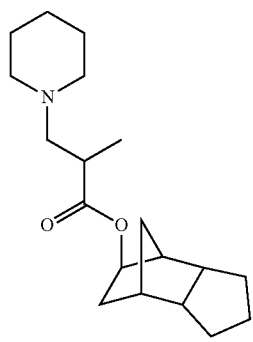 (i-3)
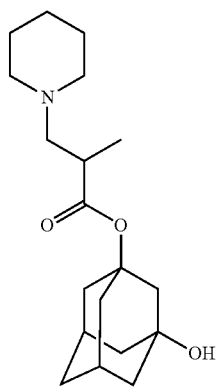 (i-4)
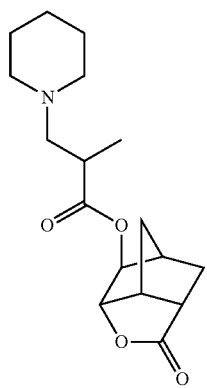 (i-5)
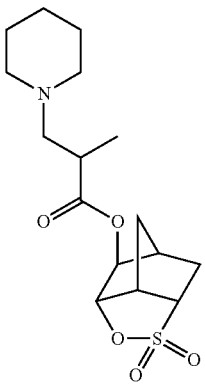 (i-6)
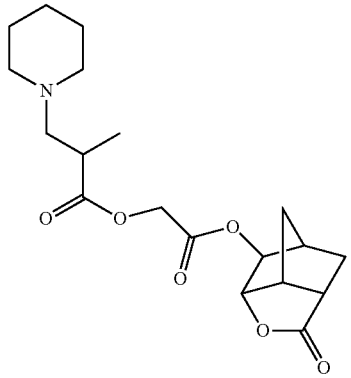 (i-7)
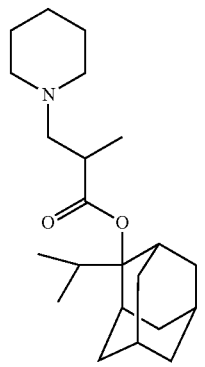 (i-8)
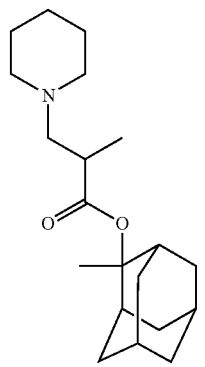 (i-9)

(i-10)
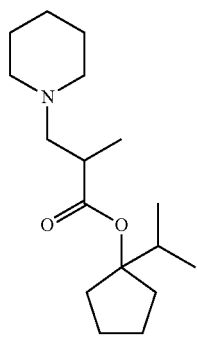
(i-11)
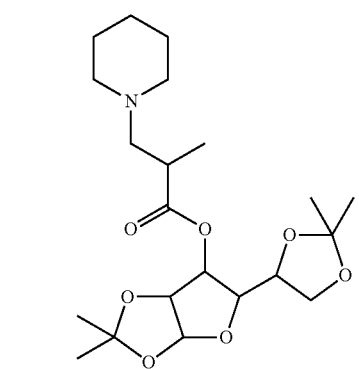
(i-12)
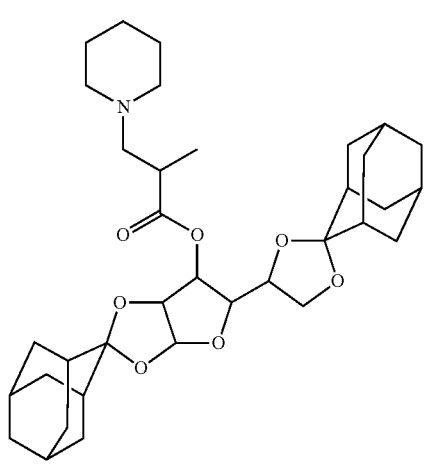
(i-13)
(i-14)
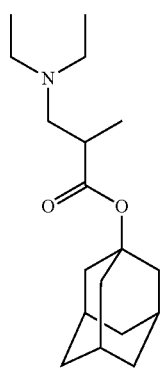
(i-15)
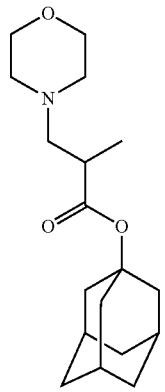
(i-16)
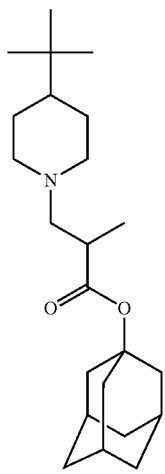
(i-17)
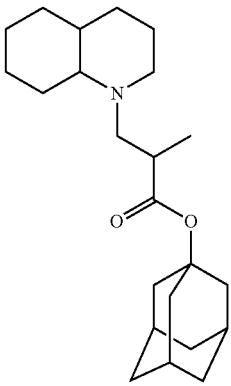

-continued

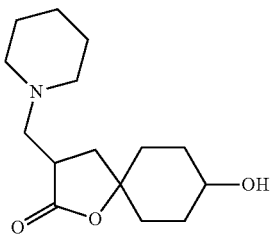
(ii-1)

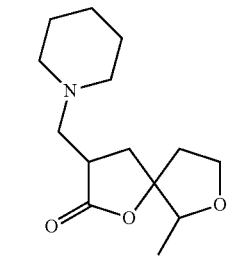
(ii-2)

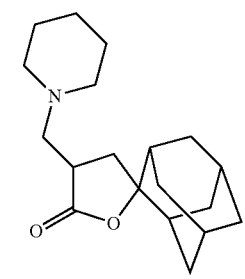
(ii-3)

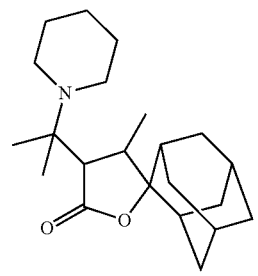
(ii-4)

Synthesis of Polymers

Each monomer used for the syntheses of the polymer (A) and the fluorine atom-containing polymer (E) is shown below.

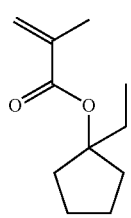
(M-1)

-continued

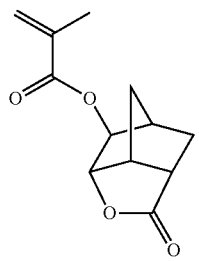
(M-2)

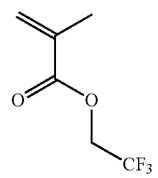
(M-3)

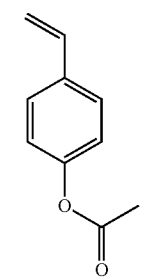
(M-4)

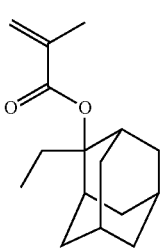
(M-5)

Synthesis of Polymer (A)

Synthesis Example 1

A monomer solution was prepared by dissolving 9.01 g (50 mol %) of the compound (M-1) and 10.99 g (50 mol %) of the compound (M-2) in 40 g of 2-butanone, and further dissolving 0.81 g (5 mol % with respect to the total number of moles of the compounds) of AIBN as a radical initiator. Subsequently, 20 g of 2-butanone was charged into a 100 mL three-neck flask, and then the three-neck flask was purged with a nitrogen gas for 30 min. Thereafter, the mixture was heated to 80° C. while stirring, and the monomer solution prepared above was added dropwise over 3 hours with a dropping funnel. The time of the start of the dropwise addition was regarded as the time of the start of the polymerization reaction, and the polymerization reaction was allowed to proceed for 6 hours. After completing the polymerization reaction, the polymerization reaction solution was water-cooled to 30° C. or below. The cooled polymerization reaction solution was poured into 400 g of methanol, and a precipitated white powder was filtered off. The filtered white powder was washed twice with each 80 g of methanol, then filtered, and thereafter dried at 50° C. for 17 hours to give a white powdery polymer (A-1) (15.6 g; yield: 78%). The polymer (A-1) had an Mw of 7,200 and an Mw/Mn of 1.52. The result of $^{13}$C-NMR analysis indicated that the proportions of the structural unit derived from (M-1) and the structural unit derived from (M-2) were 50.2 mol % and 49.8 mol %, respectively. The percentage content of the low-molecular weight matter in the polymer (A-1) was 0.04% by mass.

Synthesis Example 2

After 55.0 g of the compound (M-4) and 45.0 g of the compound (M-5), 4 g of AIBN as well as 1 g of t-dodecyl mercaptan as a chain transfer agent were dissolved in 100 g of propylene glycol monomethyl ether, the polymerization was allowed to proceed for 16 hours under a nitrogen atmosphere, while maintaining the reaction temperature of 70° C. After completing the polymerization reaction, the polymerization reaction was added dropwise into 1,000 g of n-hexane, and a polymer produced was solidified and purified. Then, after 150 g of propylene glycol monomethyl ether was again added to the polymer, 150 g of methanol, 34 g of triethylamine and 6 g of water were further added, and the hydrolysis reaction was allowed to proceed for 8 hours while the mixture was refluxed at the boiling point thereof. After completing the reaction, the solvent and triethylamine were distilled under vacuum. The obtained polymer was dissolved in 150 g of acetone, and then added dropwise into 2,000 g of water to permit solidification. The formed white powder was filtered, dried at 50° C. for 17 hours to give a polymer (A-2) as a white powder (65.7 g; yield: 76.6%). The polymer (A-2) had an Mw of 10,000 and an Mw/Mn of 2.1. The result of $^{13}$C-NMR analysis indicated that the proportions of the structural unit derived from p-hydroxystyrene and the structural unit derived from the compound (M-5) were 65.4 mol % and 34.6 mol %, respectively. The percentage content of the low-molecular weight matter in the polymer (A-2) was 0.05% by mass.

Synthesis of Fluorine Atom-Containing Polymer (E)

Synthesis Example 3

A monomer solution was prepared by dissolving 79.9 g (70 mol %) of the compound (M-1) and 20.91 g (30 mol %) of the compound (M-3) in 100 g of 2-butanone, and further dissolving 4.77 g of dimethyl 2,2'-azobisisobutyrate as a radical polymerization initiator. A 1,000 mL three-neck flask containing 100 g of 2-butanone was purged with a nitrogen gas for 30 min, and then the monomer solution prepared above was added dropwise over 3 hours with a dropping funnel with heating at 80° C. and stirring. The time of the start of the dropwise addition was regarded as the time of the start of the polymerization reaction, and the polymerization reaction was allowed to proceed for 6 hours. After completing the polymerization reaction, the polymerization reaction solution was water-cooled to 30° C. or below. After the polymerization reaction solution was transferred to a 2 L separatory funnel, the polymerization polymerization solution was homogeneously diluted with 150 g of n-hexane, and 600 g of methanol was charged, followed by mixing. Then, 30 g of distilled water was charged, followed by further shaking, and the mixture was left to stand for 30 min. Next, the lower layer was recovered and then the solvent was substituted to give a propylene glycol monomethyl ether acetate solution of a polymer (E-1) (yield: 60%). The obtained polymer (E-1) had an Mw of 7,200 and an Mw/Mn of 2.00. The result of $^{13}$C-NMR analysis indicated that the proportions of the structural unit derived from (M-1) and the structural unit derived from (M-3) were 71.1 mol % and 28.9 mol %, respectively. The percentage content of the low-molecular weight matter in the polymer (E-1) was 0.07% by mass.

Preparation of Radiation-Sensitive Resin Composition

Each component used in the preparation of each radiation-sensitive resin composition is shown below.
(B) Acid Generating Agent
B-1: triphenylsulfonium 2-(adamantan-1-ylcarbonyloxy)-1,1,3,3,3-pentafluoropropane-1-sulfonate (a compound represented by the following formula (B-1))
B-2: triphenylsulfonium norbornanesulton-2-yloxycarbonyldifluoromethanesulfonate (a compound represented by the following formula (B-2))
B-3: triphenylsulfonium 3-(piperidin-1-ylsulfonyl)-1,1,2,2,3,3-hexafluoropropane-1-sulfonate (a compound represented by the following formula (B-3))
B-4: triphenylsulfonium adamantan-1-yloxycarbonyldifluoromethanesulfonate (a compound represented by the following formula (B-4))

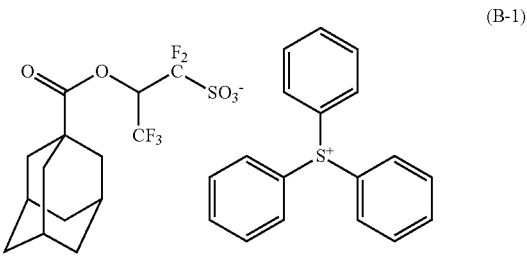

(B-1)

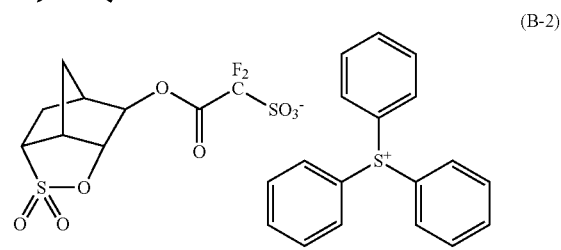

(B-2)

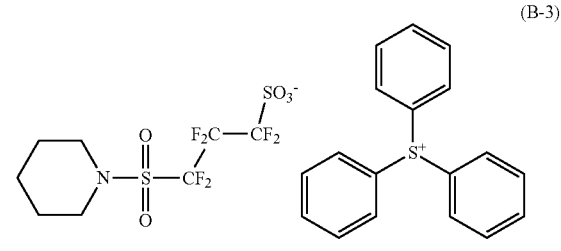

(B-3)

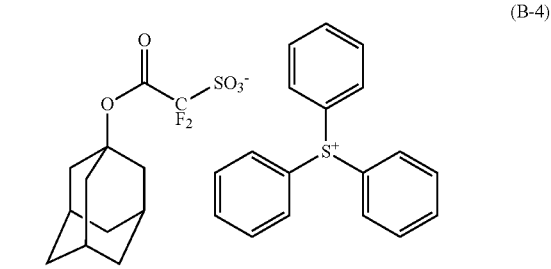

(B-4)

(C) Acid Diffusion Control Agent

Compounds represented by the above formulae (i-1) to (i-17), compounds represented by the above formulae (ii-1) to (ii-4), and compounds represented by the following formula (ci-1), formula (cii-1), formula (ciii-1), formula (civ-1) and formula (cv-1)

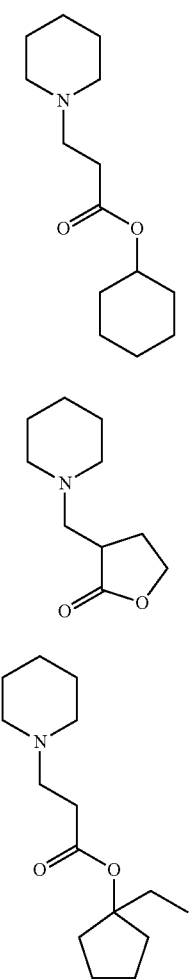

(ci-1)

(cii-1)

(ciii-1)

(civ-1)

(cv-1)

(F) Solvent
F-1: propylene glycol monomethyl ether acetate
F-2: cyclohexanone (G) Uneven Distribution Accelerator
G-1: γ-butyrolactone Example 22

A radiation-sensitive resin composition (J-1) was prepared by mixing 100 parts by mass of (A-1) as the polymer (A), 8.5 parts by mass of (B-1) as the acid generating agent (B), 30 mol % (molar ratio with respect to the acid generating agent (B)) of (i-1) as the acid diffusion control agent (C), 3 parts by mass of (E-1) as the fluorine atom-containing polymer (E), 2,240 parts by mass of (F-1) and 960 parts by mass of (F-2) as the solvent (F), and 30 parts by mass of (G-1) as the uneven distribution accelerator (G).

Examples 23 to 57 and Comparative Examples 1 to 5

Radiation-sensitive resin compositions (J-2) to (J-57) and (CJ-1) to (CJ-5) were prepared in a similar manner to Example 22 except that each component of the type and the content shown in Tables 1-1 and 1-2 was used.

TABLE 1-1

| | Radiation-sensitive resin composition | Formulation | | | | | | | | | | |
|---|---|---|---|---|---|---|---|---|---|---|---|---|
| | | (A) polymer | | (B) acid generating agent | | (C) acid diffusion control agent | | (E) fluorine atom-containing polymer | | (F) solvent | | (G) uneven distribution accelerator |
| | | | content | | content | | content | | content | | content | | content |
| | | type | (parts by mass) | type | (parts by mass) | type | (mol %) | type | (parts by mass) | type | (parts by mass) | type | (parts by mass) |
| Example 22 | J-1 | A-1 | 100 | B-1 | 8.5 | i-1 | 30 | E-1 | 3 | F-1/F-2 | 2,240/960 | G-1 | 30 |
| Example 23 | J-2 | A-1 | 100 | B-1 | 8.5 | i-2 | 30 | E-1 | 3 | F-1/F-2 | 2,240/960 | G-1 | 30 |

TABLE 1-1-continued

| Radiation-sensitive resin composition | (A) polymer type | content (parts by mass) | (B) acid generating agent type | content (parts by mass) | (C) acid diffusion control agent type | content (mol %) | (E) fluorine atom-containing polymer type | content (parts by mass) | (F) solvent type | content (parts by mass) | (G) uneven distribution accelerator type | content (parts by mass) |
|---|---|---|---|---|---|---|---|---|---|---|---|---|
| Example 24 | J-3 | A-1 | 100 | B-1 | 8.5 | i-3 | 30 | E-1 | 3 | F-1/F-2 | 2,240/960 | G-1 | 30 |
| Example 25 | J-4 | A-1 | 100 | B-1 | 8.5 | i-4 | 30 | E-1 | 3 | F-1/F-2 | 2,240/960 | G-1 | 30 |
| Example 26 | J-5 | A-1 | 100 | B-1 | 8.5 | i-5 | 30 | E-1 | 3 | F-1/F-2 | 2,240/960 | G-1 | 30 |
| Example 27 | J-6 | A-1 | 100 | B-1 | 8.5 | i-6 | 30 | E-1 | 3 | F-1/F-2 | 2,240/960 | G-1 | 30 |
| Example 28 | J-7 | A-1 | 100 | B-1 | 8.5 | i-7 | 30 | E-1 | 3 | F-1/F-2 | 2,240/960 | G-1 | 30 |
| Example 29 | J-8 | A-1 | 100 | B-1 | 8.5 | i-8 | 30 | E-1 | 3 | F-1/F-2 | 2,240/960 | G-1 | 30 |
| Example 30 | J-9 | A-1 | 100 | B-1 | 8.5 | i-9 | 30 | E-1 | 3 | F-1/F-2 | 2,240/960 | G-1 | 30 |
| Example 31 | J-10 | A-1 | 100 | B-1 | 8.5 | i-10 | 30 | E-1 | 3 | F-1/F-2 | 2,240/960 | G-1 | 30 |
| Example 32 | J-11 | A-1 | 100 | B-1 | 8.5 | i-11 | 30 | E-1 | 3 | F-1/F-2 | 2,240/960 | G-1 | 30 |
| Example 33 | J-12 | A-1 | 100 | B-1 | 8.5 | i-12 | 30 | E-1 | 3 | F-1/F-2 | 2,240/960 | G-1 | 30 |
| Example 34 | J-13 | A-1 | 100 | B-1 | 8.5 | i-13 | 30 | E-1 | 3 | F-1/F-2 | 2,240/960 | G-1 | 30 |
| Example 35 | J-14 | A-1 | 100 | B-1 | 8.5 | i-14 | 30 | E-1 | 3 | F-1/F-2 | 2,240/960 | G-1 | 30 |
| Example 36 | J-15 | A-1 | 100 | B-1 | 8.5 | i-15 | 30 | E-1 | 3 | F-1/F-2 | 2,240/960 | G-1 | 30 |
| Example 37 | J-16 | A-1 | 100 | B-1 | 8.5 | i-16 | 30 | E-1 | 3 | F-1/F-2 | 2,240/960 | G-1 | 30 |
| Example 38 | J-17 | A-1 | 100 | B-1 | 8.5 | i-17 | 30 | E-1 | 3 | F-1/F-2 | 2,240/960 | G-1 | 30 |
| Example 39 | J-18 | A-1 | 100 | B-1 | 8.5 | ii-1 | 30 | E-1 | 3 | F-1/F-2 | 2,240/960 | G-1 | 30 |
| Example 40 | J-19 | A-1 | 100 | B-1 | 8.5 | ii-2 | 30 | E-1 | 3 | F-1/F-2 | 2,240/960 | G-1 | 30 |
| Example 41 | J-20 | A-1 | 100 | B-1 | 8.5 | ii-3 | 30 | E-1 | 3 | F-1/F-2 | 2,240/960 | G-1 | 30 |
| Example 42 | J-21 | A-1 | 100 | B-1 | 8.5 | ii-4 | 30 | E-1 | 3 | F-1/F-2 | 2,240/960 | G-1 | 30 |
| Example 43 | J-22 | A-1 | 100 | B-2 | 8.5 | i-1 | 30 | E-1 | 3 | F-1/F-2 | 2,240/960 | G-1 | 30 |
| Example 44 | J-23 | A-1 | 100 | B-2 | 8.5 | i-2 | 30 | E-1 | 3 | F-1/F-2 | 2,240/960 | G-1 | 30 |
| Example 45 | J-24 | A-1 | 100 | B-2 | 8.5 | i-4 | 30 | E-1 | 3 | F-1/F-2 | 2,240/960 | G-1 | 30 |

TABLE 1-2

| Radiation-sensitive resin composition | (A) polymer type | content (parts by mass) | (B) acid generating agent type | content (parts by mass) | (C) acid diffusion control agent type | content (mol %) | (E) fluorine atom-containing polymer type | content (parts by mass) | (F) solvent type | content (parts by mass) | (G) uneven distribution accelerator type | content (parts by mass) |
|---|---|---|---|---|---|---|---|---|---|---|---|---|
| Example 46 | J-25 | A-1 | 100 | B-2 | 8.5 | i-10 | 30 | E-1 | 3 | F-1/F-2 | 2,240/960 | G-1 | 30 |
| Example 47 | J-26 | A-1 | 100 | B-2 | 8.5 | i-17 | 30 | E-1 | 3 | F-1/F-2 | 2,240/960 | G-1 | 30 |
| Example 48 | J-27 | A-1 | 100 | B-3 | 8.5 | i-1 | 30 | E-1 | 3 | F-1/F-2 | 2,240/960 | G-1 | 30 |
| Example 49 | J-28 | A-1 | 100 | B-3 | 8.5 | i-2 | 30 | E-1 | 3 | F-1/F-2 | 2,240/960 | G-1 | 30 |
| Example 50 | J-29 | A-1 | 100 | B-3 | 8.5 | i-4 | 30 | E-1 | 3 | F-1/F-2 | 2,240/960 | G-1 | 30 |
| Example 51 | J-30 | A-1 | 100 | B-3 | 8.5 | i-10 | 30 | E-1 | 3 | F-1/F-2 | 2,240/960 | G-1 | 30 |
| Example 52 | J-31 | A-1 | 100 | B-3 | 8.5 | i-17 | 30 | E-1 | 3 | F-1/F-2 | 2,240/960 | G-1 | 30 |
| Example 53 | J-32 | A-1 | 100 | B-4 | 8.5 | i-1 | 30 | E-1 | 3 | F-1/F-2 | 2,240/960 | G-1 | 30 |
| Example 54 | J-33 | A-1 | 100 | B-4 | 8.5 | i-2 | 30 | E-1 | 3 | F-1/F-2 | 2,240/960 | G-1 | 30 |
| Example 55 | J-34 | A-1 | 100 | B-4 | 8.5 | i-4 | 30 | E-1 | 3 | F-1/F-2 | 2,240/960 | G-1 | 30 |
| Example 56 | J-35 | A-1 | 100 | B-4 | 8.5 | i-10 | 30 | E-1 | 3 | F-1/F-2 | 2,240/960 | G-1 | 30 |
| Example 57 | J-36 | A-1 | 100 | B-4 | 8.5 | i-17 | 30 | E-1 | 3 | F-1/F-2 | 2,240/960 | G-1 | 30 |
| Comparative Example 1 | CJ-1 | A-1 | 100 | B-1 | 8.5 | ci-1 | 30 | E-1 | 3 | F-1/F-2 | 2,240/960 | G-1 | 30 |
| Comparative Example 2 | CJ-2 | A-1 | 100 | B-1 | 8.5 | cii-1 | 30 | E-1 | 3 | F-1/F-2 | 2,240/960 | G-1 | 30 |
| Comparative Example 3 | CJ-3 | A-1 | 100 | B-2 | 8.5 | ciii-1 | 30 | E-1 | 3 | F-1/F-2 | 2,240/960 | G-1 | 30 |
| Comparative Example 4 | CJ-4 | A-1 | 100 | B-3 | 8.5 | civ-1 | 30 | E-1 | 3 | F-1/F-2 | 2,240/960 | G-1 | 30 |
| Comparative Example 5 | CJ-5 | A-1 | 100 | B-4 | 8.5 | cv-1 | 30 | E-1 | 3 | F-1/F-2 | 2,240/960 | G-1 | 30 |

Formation of Resist Pattern
Use of ArF Exposure
Development with Alkali

An underlayer antireflective film having a film thickness of 105 nm was provided on the surface of a 12-inch silicon wafer by coating a composition for forming an underlayer antireflective film (ARC66, manufactured by Brewer Science) with a spin coater (CLEAN TRACK ACT12, manufactured by Tokyo Electron Limited), and thereafter subjecting the same to heating at 205° C. for 60 sec. Then, each radiation-sensitive resin composition was coated on the underlayer antireflective film using the spin coater, and thereafter subjected to PB at 90° C. for 60 sec. Subsequently, cooling was carried out at 23° C. for 30 sec to provide a resist film having a film thickness of 90 nm. Next, the resist film was exposed through a 40 nm line-and-space (1L 1S) mask pattern using an ArF Excimer Laser Immersion Scanner (NSR-S610C, manufactured by Nikon corporation) under optical conditions involving NA of 1.3 and dipole (Sigma being 0.977/0.782). After the exposure, PEB was carried out at 90° C. for 60 sec. Thereafter, a development was carried out using a 2.38% by mass aqueous TMAH solution, followed by washing with water and drying to form a positive type resist pattern.

Development with Organic Solvent

A negative type resist pattern was formed in a similar manner to that in "Development with Alkali" above except that n-butyl acetate was used in place of the 2.38% by mass aqueous TMAH solution as the developer solution, and that washing with water was not conducted in forming the resist pattern with the above "Development with Alkali".

Evaluations

In each of the above cases of "Development with Alkali" and "Development with Organic Solvent", each radiation-sensitive resin composition was evaluated by determination on each resist pattern formed. In each case described above, an exposure dose at which 40 nm 1L 1S pattern was formed by an exposure through the 40 nm 1L 1S mask pattern was defined as an optimum exposure dose (Eop). It is to be noted that a scanning electron microscope (S-9380; manufactured by Hitachi High-Technologies Corporation) was used for the measurement on the resist pattern formed according to this method. In the evaluations below, comparisons of Examples were made with: Comparative Example 1 for Examples 22 to 38; Comparative Example 2 for Examples 39 to 42; Comparative Example 3 for Examples 43 to 47; Comparative Example 4 for Examples 48 to 52; and Comparative Example 5 for Examples 53 to 57. The results of the evaluations are shown in Table 2-1 and Table 2-2. In Tables 2-1 and 2-2, "-" denotes being a decision standard.

LWR Performance

The resist pattern formed at Eop described above was observed from above the pattern using the scanning electron microscope. The line width was measured at arbitrary points of 50 in total, and a 3 Sigma value was determined from the distribution of the measurements, and the value was defined as an indicative of the LWR performance (nm). The smaller value indicates a better LWR performance. As compared with the Comparative Example, the evaluation of the LWR performance was made as: "A" when an improvement of the LWR performance of no less than 10% (i.e., the value of the LWR performance being no greater than 90%) was found; "B" when an improvement of the LWR performance of no less than 5% and less than 10% was found; and "C" when an improvement of the LWR performance of less than 5% was found.

Resolution

A dimension of the minimum resist pattern which was resolved at the Eop was defined as an indicative of the resolution (nm). The smaller measurement indicates a better resolution. As compared with the Comparative Example, the evaluation of the resolution was made as: "A" when an improvement of the resolution of no less than 10% (i.e., the value of the resolution being no greater than 90%) was found; "B" when an improvement of the resolution of no less than 5% and less than 10% was found; and "C" when an improvement of the resolution of less than 5% was found.

Rectangularity of the Cross-Sectional Shape

A cross-sectional shape of the resist pattern which was resolved at the Eop was observed to measure a line width Lb at the middle along an altitude direction of the resist pattern, and a line width La on the top of the film. The rectangularity of the cross-sectional shape was evaluated as: "A" (favorable) in a case where 0.9≤La/Lb≤1.1; and as "B" (unfavorable) in a case where (La/Lb)<0.9 or 1.1<(La/Lb).

Depth of Focus

On the resist pattern which was resolved at the Eop, the dimension when the focus was shifted along the depth direction was observed, and the depth of focus was defined as a latitude in the depth direction in which the pattern dimension falls within the range of 90% to 110% of the standard without being accompanied by a bridge and/or residue. The greater depth of focus (nm) is more favorable. As compared with the Comparative Example, the evaluation of the depth of focus was made as: "A" when an improvement of the depth of focus of no less than 10% (i.e., the value of the depth of focus being no less than 110%) was found; "B" when an improvement of the depth of focus of no less than 5% and less than 10% was found; and "C" when an improvement of the depth of focus of less than 5% was found.

TABLE 2-1

| | Radiation-sensitive resin composition | Development with an alkali | | | | Development with an organic solvent | | | |
| | | LWR performance | resolution | rectangularity of cross-sectional shape | depth of focus | LWR performance | resolution | rectangularity of cross-sectional shape | depth of focus |
| --- | --- | --- | --- | --- | --- | --- | --- | --- | --- |
| Example 22 | J-1 | A | A | A | A | A | A | A | A |
| Example 23 | J-2 | A | A | A | A | A | A | A | A |
| Example 24 | J-3 | B | B | A | B | B | B | A | B |
| Example 25 | J-4 | A | A | A | A | A | A | A | A |
| Example 26 | J-5 | B | B | A | B | B | B | A | B |
| Example 27 | J-6 | B | B | A | B | B | B | A | B |
| Example 28 | J-7 | B | B | A | B | B | B | A | B |
| Example 29 | J-8 | B | B | A | B | B | B | A | B |
| Example 30 | J-9 | B | B | A | B | B | B | A | B |
| Example 31 | J-10 | A | A | A | A | A | A | A | A |
| Example 32 | J-11 | B | B | A | B | B | B | A | B |
| Example 33 | J-12 | B | B | A | B | B | B | A | B |
| Example 34 | J-13 | B | B | A | B | B | B | A | B |
| Example 35 | J-14 | B | B | A | B | B | B | A | B |
| Example 36 | J-15 | B | B | A | B | B | B | A | B |
| Example 37 | J-16 | B | B | A | B | B | B | A | B |

TABLE 2-1-continued

| | Radiation-sensitive resin composition | Development with an alkali | | | | Development with an organic solvent | | | |
|---|---|---|---|---|---|---|---|---|---|
| | | LWR performance | resolution | rectangularity of cross-sectional shape | depth of focus | LWR performance | resolution | rectangularity of cross-sectional shape | depth of focus |
| Example 38 | J-17 | A | A | A | A | A | A | A | A |
| Example 39 | J-18 | A | A | A | A | A | A | A | A |
| Example 40 | J-19 | A | A | A | A | A | A | A | A |
| Example 41 | J-20 | B | B | A | B | B | B | A | B |
| Example 42 | J-21 | B | B | A | B | B | B | A | B |
| Example 43 | J-22 | A | A | A | A | A | A | A | A |
| Example 44 | J-23 | A | A | A | A | A | A | A | A |

TABLE 2-2

| | Radiation-sensitive resin composition | Development with an alkali | | | | Development with an organic solvent | | | |
|---|---|---|---|---|---|---|---|---|---|
| | | LWR performance | resolution | rectangularity of cross-sectional shape | depth of focus | LWR performance | resolution | rectangularity of cross-sectional shape | depth of focus |
| Example 45 | J-24 | A | A | A | A | A | A | A | A |
| Example 46 | J-25 | A | A | A | A | A | A | A | A |
| Example 47 | J-26 | A | A | A | A | A | A | A | A |
| Example 48 | J-27 | A | A | A | A | A | A | A | A |
| Example 49 | J-28 | A | A | A | A | A | A | A | A |
| Example 50 | J-29 | A | A | A | A | A | A | A | A |
| Example 51 | J-30 | A | A | A | A | A | A | A | A |
| Example 52 | J-31 | A | A | A | A | A | A | A | A |
| Example 53 | J-32 | A | A | A | A | A | A | A | A |
| Example 54 | J-33 | A | A | A | A | A | A | A | A |
| Example 55 | J-34 | A | A | A | A | A | A | A | A |
| Example 56 | J-35 | A | A | A | A | A | A | A | A |
| Example 57 | J-36 | A | A | A | A | A | A | A | A |
| Comparative Example 1 | CJ-1 | — | — | B | — | — | — | B | — |
| Comparative Example 2 | CJ-2 | — | — | B | — | — | — | B | — |
| Comparative Example 3 | CJ-3 | — | — | B | — | — | — | B | — |
| Comparative Example 4 | CJ-4 | — | — | B | — | — | — | B | — |
| Comparative Example 5 | CJ-5 | — | — | B | — | — | — | B | — |

As is clear from the results shown in Tables 2-1 and 2-2, in the case of the ArF exposure, the radiation-sensitive resin compositions of Examples exhibited favorable LWR performance, resolution, rectangularity of the cross-sectional shape and depth of focus, as compared with the radiation-sensitive resin compositions of Comparative Examples whether the development was carried out with an alkali or an organic solvent.

Preparation of Radiation-Sensitive Resin Composition

Use of Irradiation with Electron Beam

Example 58

A radiation-sensitive resin composition (J-37) was prepared by mixing 100 parts by mass of (A-2) as the polymer (A), 20 parts by mass of (B-1) as the acid generating agent (B), 30 mol % (molar ratio with respect to the acid generating agent (B)) of (i-1) as the acid diffusion control agent (C), and 4,280 parts by mass of (F-1) and 1,830 parts by mass of (F-2) as the solvent (F).

Examples 59 to 93 and Comparative Examples 6 to 10

Radiation-sensitive resin compositions (J-38) to (J-72) and (CJ-6) to (CJ-10) were prepared in a similar manner to Example 58 except that each component of the type and the content shown in Tables 3-1, 3-2, and 3-3 was used.

Formation of Resist Pattern

Each radiation-sensitive resin composition shown in Tables 3-1, 3-2, and 3-3 below was coated on the surface of an 8-inch silicon wafer using a spin coater (CLEAN TRACK ACT8, manufactured by Tokyo Electron Limited), and subjected to PB at 90° C. for 60 sec. Thereafter, cooling at 23° C. for 30 sec gave a resist film having a film thickness of 50 nm. Next, this resist film was irradiated with an electron beam using a simplified electron beam writer (HL800D, manufactured by Hitachi, Ltd., power: 50 KeV, electric current density: 5.0 ampere/cm²). After the irradiation, PEB was carried out at 130° C. for 60 sec. Thereafter, a development was carried out using a 2.38% by mass aqueous TMAH solution at 23° C. for 30 sec, followed by washing with water and drying to form a positive type resist pattern.

Evaluations

The radiation-sensitive resin compositions were evaluated on the LWR performance, the resolution and the rectangularity of the cross-sectional shape of each resist pattern formed, among the evaluations in "Use of ArF Exposure" above, in accordance with each method similar to that for the determination described above. Comparisons of Examples were made with: Comparative Example 6 for Examples 58 to 74; Comparative Example 7 for Examples 75 to 78; Comparative Example 8 for Examples 79 to 83; Comparative Example 9 for Examples 84 to 88; and Comparative Example 10 for Examples 89 to 93. The results of the evaluations are shown in Tables 3-1, 3-2, and 3-2 altogether. In Tables 3-1, 3-2, and 3-3, "-" denotes being a decision standard.

TABLE 3-1

| | | | | Formulation | | | | | | Evaluation results | | |
| | | | | | (B) acid generating agent | | (C) acid diffusion control agent | | (F) solvent | | | | Rectangularity of the cross-sectional shape |
| | Radiation-sensitive resin composition | (A) polymer type | content. (parts by mass) | type | content (parts by mass) | type | content (mol %) | type | content (parts by mass) | LWR performance | resolution | |
|---|---|---|---|---|---|---|---|---|---|---|---|---|
| Example 58 | J-37 | A-2 | 100 | B-1 | 20 | i-1 | 30 | F-1/F-2 | 4,280/1,830 | A | A | A |
| Example 59 | J-38 | A-2 | 100 | B-1 | 20 | i-2 | 30 | F-1/F-2 | 4,280/1,830 | A | A | A |
| Example 60 | J-39 | A-2 | 100 | B-1 | 20 | i-3 | 30 | F-1/F-2 | 4,280/1,830 | B | B | A |
| Example 61 | J-40 | A-2 | 100 | B-1 | 20 | i-4 | 30 | F-1/F-2 | 4,280/1,830 | A | A | A |
| Example 62 | J-41 | A-2 | 100 | B-1 | 20 | i-5 | 30 | F-1/F-2 | 4,280/1,830 | B | B | A |
| Example 63 | J-42 | A-2 | 100 | B-1 | 20 | i-6 | 30 | F-1/F-2 | 4,280/1,830 | B | B | A |
| Example 64 | J-43 | A-2 | 100 | B-1 | 20 | i-7 | 30 | F-1/F-2 | 4,280/1,830 | B | B | A |
| Example 65 | J-44 | A-2 | 100 | B-1 | 20 | i-8 | 30 | F-1/F-2 | 4,280/1,830 | B | B | A |
| Example 66 | J-45 | A-2 | 100 | B-1 | 20 | i-9 | 30 | F-1/F-2 | 4,280/1,830 | B | B | A |
| Example 67 | J-46 | A-2 | 100 | B-1 | 20 | i-10 | 30 | F-1/F-2 | 4,280/1,830 | A | A | A |
| Example 68 | J-47 | A-2 | 100 | B-1 | 20 | i-11 | 30 | F-1/F-2 | 4,280/1,830 | B | B | A |
| Example 69 | J-48 | A-2 | 100 | B-1 | 20 | i-12 | 30 | F-1/F-2 | 4,280/1,830 | B | B | A |
| Example 70 | J-49 | A-2 | 100 | B-1 | 20 | i-13 | 30 | F-1/F-2 | 4,280/1,830 | B | B | A |
| Example 71 | J-50 | A-2 | 100 | B-1 | 20 | i-14 | 30 | F-1/F-2 | 4,280/1,830 | B | B | A |

TABLE 3-2

| | | | | Formulation | | | | | | Evaluation results | | |
| | | | | | (B) acid generating agent | | (C) acid diffusion control agent | | (F) solvent | | | | Rectangularity of the cross-sectional shape |
| | Radiation-sensitive resin composition | (A) polymer type | content. (parts by mass) | type | content (parts by mass) | type | content (mol %) | type | content (parts by mass) | LWR performance | resolution | |
|---|---|---|---|---|---|---|---|---|---|---|---|---|
| Example 72 | J-51 | A-2 | 100 | B-1 | 20 | i-15 | 30 | F-1/F-2 | 4,280/1,830 | B | B | A |
| Example 73 | J-52 | A-2 | 100 | B-1 | 20 | i-16 | 30 | F-1/F-2 | 4,280/1,830 | B | B | A |
| Example 74 | J-53 | A-2 | 100 | B-1 | 20 | i-17 | 30 | F-1/F-2 | 4,280/1,830 | A | A | A |
| Example 75 | J-54 | A-2 | 100 | B-1 | 20 | ii-1 | 30 | F-1/F-2 | 4,280/1,830 | A | A | A |
| Example 76 | J-55 | A-2 | 100 | B-1 | 20 | ii-2 | 30 | F-1/F-2 | 4,280/1,830 | A | A | A |
| Example 77 | J-56 | A-2 | 100 | B-1 | 20 | ii-3 | 30 | F-1/F-2 | 4,280/1,830 | B | B | A |
| Example 78 | J-57 | A-2 | 100 | B-1 | 20 | ii-4 | 30 | F-1/F-2 | 4,280/1,830 | B | B | A |
| Example 79 | J-58 | A-2 | 100 | B-2 | 20 | i-1 | 30 | F-1/F-2 | 4,280/1,830 | A | A | A |
| Example 80 | J-59 | A-2 | 100 | B-2 | 20 | i-2 | 30 | F-1/F-2 | 4,280/1,830 | A | A | A |
| Example 81 | J-60 | A-2 | 100 | B-2 | 20 | i-4 | 30 | F-1/F-2 | 4,280/1,830 | A | A | A |
| Example 82 | J-61 | A-2 | 100 | B-2 | 20 | i-10 | 30 | F-1/F-2 | 4,280/1,830 | A | A | A |
| Example 83 | J-62 | A-2 | 100 | B-2 | 20 | i-17 | 30 | F-1/F-2 | 4,280/1,830 | A | A | A |
| Example 84 | J-63 | A-2 | 100 | B-3 | 20 | i-1 | 30 | F-1/F-2 | 4,280/1,830 | A | A | A |

TABLE 3-3

| | Radiation-sensitive resin composition | (A) polymer | | (B) acid generating agent | | (C) acid diffusion control agent | | (F) solvent | | Evaluation results | | |
|---|---|---|---|---|---|---|---|---|---|---|---|---|
| | | type | content. (parts by mass) | type | content (parts by mass) | type | content (mol %) | type | content (parts by mass) | LWR performance | resolution | Rectangularity of the cross-sectional shape |
| Example 85 | J-64 | A-2 | 100 | B-3 | 20 | i-2 | 30 | F-1/F-2 | 4,280/1,830 | A | A | A |
| Example 86 | J-65 | A-2 | 100 | B-3 | 20 | i-4 | 30 | F-1/F-2 | 4,280/1,830 | A | A | A |
| Example 87 | J-66 | A-2 | 100 | B-3 | 20 | i-10 | 30 | F-1/F-2 | 4,280/1,830 | A | A | A |
| Example 88 | J-67 | A-2 | 100 | B-3 | 20 | i-17 | 30 | F-1/F-2 | 4,280/1,830 | A | A | A |
| Example 89 | J-68 | A-2 | 100 | B-4 | 20 | i-1 | 30 | F-1/F-2 | 4,280/1,830 | A | A | A |
| Example 90 | J-69 | A-2 | 100 | B-4 | 20 | i-2 | 30 | F-1/F-2 | 4,280/1,830 | A | A | A |
| Example 91 | J-70 | A-2 | 100 | B-4 | 20 | i-4 | 30 | F-1/F-2 | 4,280/1,830 | A | A | A |
| Example 92 | J-71 | A-2 | 100 | B-4 | 20 | i-10 | 30 | F-1/F-2 | 4,280/1,830 | A | A | A |
| Example 93 | J-72 | A-2 | 100 | B-4 | 20 | i-17 | 30 | F-1/F-2 | 4,280/1,830 | A | A | A |
| Comparative Example 6 | CJ-6 | A-2 | 100 | B-1 | 20 | ci-1 | 30 | F-1/F-2 | 4,280/1,830 | — | — | B |
| Comparative Example 7 | CJ-7 | A-2 | 100 | B-1 | 20 | cii-1 | 30 | F-1/F-2 | 4,280/1,830 | — | — | B |
| Comparative Example 8 | CJ-8 | A-2 | 100 | B-2 | 20 | ciii-1 | 30 | F-1/F-2 | 4,280/1,830 | — | — | B |
| Comparative Example 9 | CJ-9 | A-2 | 100 | B-3 | 20 | civ-1 | 30 | F-1/F-2 | 4,280/1,830 | — | — | B |
| Comparative Example 10 | CJ-10 | A-2 | 100 | B-4 | 20 | cv-1 | 30 | F-1/F-2 | 4,280/1,830 | — | — | B |

As is clear from the results shown in Tables 3-1, 3-2, and 3-3, in the case where irradiation was carried out with an electron beam, the radiation-sensitive resin compositions of Examples were concluded to exhibit favorable LWR performance, resolution and rectangularity of the cross-sectional shape, as compared with the radiation-sensitive resin compositions of Comparative Examples.

According to the acid diffusion control agent, the radiation-sensitive resin composition containing the same, and the resist pattern-forming method in which the radiation-sensitive resin composition is used of the embodiments of the present invention, while exhibiting a great depth of focus, a resist pattern having small LWR, superior rectangularity of the cross-sectional shape, and high resolution can be formed. In addition, the compound according to still other embodiment of the present invention can be suitably used as the acid diffusion control agent. Therefore, these can be suitably used for pattern formation in manufacture of semiconductor devices in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:

a polymer having an acid-labile group;

an acid generator; and a first acid diffusion control agent which comprises a compound represented by formula (1), a compound represented by formula (2) or both thereof:

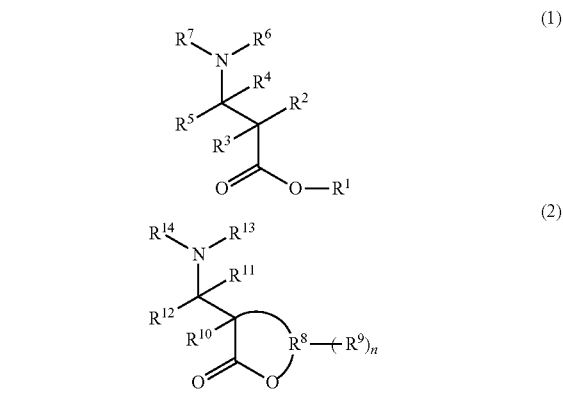

wherein, in the formula (1), $R^1$ represents an acid-nonlabile hydrocarbon group comprising a monovalent alicyclic structure and having 3 to 12 carbon atoms, a heteroatom-containing group obtained by inserting —O—, —CO—, —COO—, —SO$_2$O—, —NR$^a$SO$_2$—, —NR$^a$CO— or a combination thereof between two carbon atoms in the acid-nonlabile hydrocarbon group, or a group obtained by substituting a part or all of hydrogen atoms included in any one of the hydrocarbon group or the heteroatom-containing group with a hydroxy group, a halogen atom or a combination thereof, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms together with the nitrogen atom to which $R^6$ and $R^7$ bond;

in the formula (2), $R^8$ represents a monocyclic heterocyclic group having a valency of (n+2) and having 5 to 8 ring atoms together with the ester group to which $R^8$ bonds and with the carbon atom to which $R^{10}$ bonds;

n is an integer of 1 to 6;

$R^9$ represents a monovalent hydrocarbon group having 1 to 20 carbon atoms, a monovalent heteroatom-containing group comprising —O—, —CO—, —COO—, —SO$_2$O—, —NR$^b$SO$_2$—, —NR$^b$CO— or a combination thereof between two carbon atoms in the monovalent hydrocarbon group, or a group obtained by substituting a part or all of hydrogen atoms included in any one of the monovalent hydrocarbon group or the monovalent heteroatom-containing group with a hydroxy group, a halogen atom or a combination thereof; and optionally, in a case where n is 2 or greater, two or more $R^9$s among a plurality of $R^9$s taken together represent a ring structure having 3 to 10 ring atoms, a heterering structure comprising —O—, —CO—, —COO—, —SO$_2$O—, —NR$^b$SO$_2$—, —NR$^b$CO— or a combination thereof between two carbon atoms in the ring structure, or a group obtained by substituting a part or all of hydrogen atoms included in any one of the ring structure or the heterering structure with a hydroxy group, a halogen atom or a combination thereof, wherein $R^b$ represents a hydrogen atom or a monovalent hydrocarbon group having 1 to 10 carbon atoms;

$R^{10}$ represents a hydrogen atom or a monovalent hydrocarbon group having 1 to 10 carbon atoms;

$R^{11}$ and $R^{12}$ each independently represent a hydrogen atom or a monovalent hydrocarbon group having 1 to 10 carbon atoms; and $R^{13}$ and $R^{14}$ each independently represent a hydrogen atom or a monovalent hydrocarbon group having 1 to 10 carbon atoms, or $R^{13}$ and $R^{14}$ taken together represent a ring structure having 3 to 10 ring atoms together with the nitrogen atom to which $R^{13}$ and $R^{14}$ bond.

2. The radiation-sensitive resin composition according to claim 1, further comprising a second acid diffusion control agent other than the first acid diffusion control agent.

3. A resist pattern-forming method comprising:
applying the radiation-sensitive resin composition according to claim 1 on a substrate to provide a resist film;
exposing the resist film; and
developing the resist film exposed.

4. The radiation-sensitive resin composition according to claim 1, wherein the first acid diffusion control agent comprises the compound represented by the formula (1), and in the formula (1), at least one of $R^2$ and $R^3$ represents a hydrogen atom.

5. The radiation-sensitive resin composition according to claim 1, wherein the first acid diffusion control agent comprises the compound represented by the formula (1), and in the formula (1), each of $R^4$ and $R^5$ represents a hydrogen atom.

6. The radiation-sensitive resin composition according to claim 1, wherein the first acid diffusion control agent comprises the compound represented by the formula (1), and in the formula (1), $R^6$ and $R^7$ taken together represent the ring structure having 3 to 10 ring atoms together with the nitrogen atom to which $R^6$ and $R^7$ bond.

7. The radiation-sensitive resin composition according to claim 1, wherein the first acid diffusion control agent comprises the compound represented by the formula (2), and in the formula (2), n is 2 or greater, and two or more $R^9$s among a plurality of $R^9$s taken together represent the ring structure having 3 to 10 ring atoms, the heterering structure comprising —O—, —CO—, —COO—, —SO$_2$O—, —NR$^b$SO$_2$—, —NR$^b$CO— or a combination thereof between two carbon atoms in the ring structure, or a group obtained by substituting a part or all of hydrogen atoms included in any one of the ring structure or the heterering structure with a hydroxy group, a halogen atom or a combination thereof, wherein $R^b$ represents a hydrogen atom or a monovalent hydrocarbon group having 1 to 10 carbon atoms.

8. The radiation-sensitive resin composition according to claim 1, wherein the first acid diffusion control agent comprises the compound represented by the formula (2), and in the formula (2), $R^{13}$ and $R^{14}$ taken together represent the ring structure having 3 to 10 ring atoms together with the nitrogen atom to which $R^{13}$ and $R^{14}$ bond.

9. The radiation-sensitive resin composition according to claim 8, the ring structure or the heterering structure is a spiro ring structure.

10. A compound represented by formula (1):

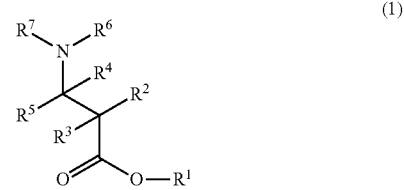

(1)

wherein, in the formula (1), $R^1$ represents an acid-nonlabile hydrocarbon group comprising a monovalent alicyclic structure and having 3 to 12 carbon atoms, a heteroatom-containing group obtained by inserting —O—, —CO—, —COO—, —SO$_2$O—, —NR$^a$SO$_2$—, —NR$^a$CO— or a combination thereof between two carbon atoms in the acid-nonlabile hydrocarbon group, or a group obtained by substituting a part or all of hydrogen atoms included in any one of the hydrocarbon group or the heteroatom-containing group with a hydroxy group, a halogen atom or a combination thereof, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms together with the nitrogen atom to which $R^6$ and $R^7$ bond.

11. The compound according to claim 10, wherein in the formula (1), at least one of $R^2$ and $R^3$ represents a hydrogen atom.

12. The compound according to claim 10, wherein in the formula (1), each of $R^4$ and $R^5$ represents a hydrogen atom.

13. The compound according to claim 10, wherein in the formula (1), $R^6$ and $R^7$ taken together represent the ring structure having 3 to 10 ring atoms together with the nitrogen atom to which $R^6$ and $R^7$ bond.

14. A production method comprising reacting a compound represented by formula (i-a) and an amine compound represented by formula (i-b) to produce a compound represented by formula (1):

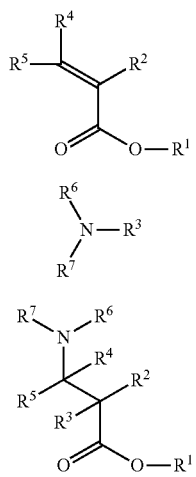

wherein, in the formulae (i-a), (i-b) and (1), $R^1$ represents an acid-nonlabile hydrocarbon group comprising a monovalent alicyclic structure and having 3 to 12 carbon atoms, a heteroatom-containing group obtained by inserting —O—, —CO—, —COO—, —SO$_2$O—, —NR$^a$SO$_2$—, —NR$^a$CO— or a combination thereof between two carbon atoms in the acid-nonlabile hydrocarbon group, or a group obtained by substituting a part or all of hydrogen atoms included in any one of the hydrocarbon group or the heteroatom-containing group with a hydroxy group, a halogen atom or a combination thereof, wherein $R^a$ represents a hydrogen atom or a hydrocarbon group having 1 to 10 carbon atoms;

$R^2$ and $R^3$ each independently represent a hydrogen atom or a monovalent hydrocarbon group having 1 to 10 carbon atoms, and at least one of $R^2$ and $R^3$ represents a monovalent hydrocarbon group having 1 to 10 carbon atoms;

$R^4$ and $R^5$ each independently represent a hydrogen atom or a monovalent hydrocarbon group having 1 to 10 carbon atoms; and $R^6$ and $R^7$ each independently represent a hydrogen atom or a monovalent hydrocarbon group having 1 to 10 carbon atoms, or $R^6$ and $R^7$ taken together represent a ring structure having 3 to 10 ring atoms together with the nitrogen atom to which $R^6$ and $R^7$ bond.

* * * * *